(12) United States Patent
Xu et al.

(10) Patent No.: US 7,022,513 B2
(45) Date of Patent: Apr. 4, 2006

(54) CELL BASED SIGNAL GENERATION

(75) Inventors: Jun Xu, Ossining, NY (US); Joshua Trueheart, South Nyack, NY (US)

(73) Assignee: Cadus Technologies, Inc., New York, NY (US)

( * ) Notice: Subject to any disclaimer, the term of this patent is extended or adjusted under 35 U.S.C. 154(b) by 370 days.

(21) Appl. No.: 10/200,013

(22) Filed: Jul. 18, 2002

(65) Prior Publication Data
US 2003/0170760 A1    Sep. 11, 2003

Related U.S. Application Data

(63) Continuation of application No. 09/241,888, filed on Feb. 1, 1999, now Pat. No. 6,504,008.

(51) Int. Cl.
C12N 1/16 (2006.01)
(52) U.S. Cl. ................ 435/255.1; 435/243; 435/254.1; 435/254.11; 435/254.2; 435/254.21; 435/255.2
(58) Field of Classification Search ................ 435/243, 435/254.1, 254.11, 254.2, 254.21, 255.1, 435/255.2
See application file for complete search history.

(56) References Cited

U.S. PATENT DOCUMENTS

| | | | |
|---|---|---|---|
| 4,418,149 A | 11/1983 | Ptashne et al. |
| 4,833,080 A | 5/1989 | Brent et al. |
| 4,948,874 A | 8/1990 | Kronvall et al. |
| 5,096,815 A | 3/1992 | Ladner et al. |
| 5,283,173 A | 2/1994 | Fields et al. |
| 5,401,629 A | 3/1995 | Harpold et al. |
| 5,436,128 A | 7/1995 | Harpold et al. |
| 5,468,614 A | 11/1995 | Fields et al. |
| 5,482,835 A | 1/1996 | King et al. |
| 5,580,736 A | 12/1996 | Brent et al. |
| 5,691,188 A | 11/1997 | Pausch et al. |
| 5,739,029 A | 4/1998 | King et al. |
| 5,789,184 A | 8/1998 | Fowlkes et al. |

FOREIGN PATENT DOCUMENTS

| | | |
|---|---|---|
| EP | 568925 | 11/1993 |
| WO | WO 88/10308 | 12/1988 |
| WO | WO 91/12273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |

OTHER PUBLICATIONS

Akada, R. et al. "Genetic Relationships Between the G Protein βγ Complex, Ste5p, Ste20p and Cdc42p: Investigation of Effector Roles in the Yeast Pheromone Response Pathway," *Genetics* 143:103-117 (1996).

Alison, Malcolm R. et al. "Growth factors and growth factor receptors," *Brit. J. of Hosp. Med.* 49(11):774-88 (1993).

Altieri, Dario C. "Proteases and protease receptors in modulation of leukocyte effector functions," *J. of Leukocyte Biol.* 58:120-27 (1995).

Artemyev, Nikolai O. et al. "Sites of Interaction between Rod G-Protein α-Subunit and cGMP-phosphodiesterase γ-Subunit," *J. Biol. Chem.* 267(35):25067-72 (1992).

Awramik, S. M. "New fossil finds in old rocks," *Nature* 319:446-47 (1986).

Belka, C. et al. "The role of tyrosine kinases and their substrates in signal transmission of hematopoietic growth factors: a short review," *Leukemia* 9:754-61 (1995).

Bender, Alan and Sprague,George F. Jr. "Pheromones and Pheromone Receptors Are the Primary Determinants of Mating Specificity in the Yeast *Saccharomyces cerevisiae*," *Genetics* 121:463-76 (1989).

Birnbaumer, Lutz "Transduction of receptor signal into modulation of effector activity by G proteins: the first 20 years or so . . . " *FASEB Journal* 4:3178-88 (1990).

Blinder, Dmitry et al. "Constitutive Mutants in the Yeast Pheromone Response: Ordered function of the Gene Products," *Cell* 56:479-486 (1989).

Brill, Julie A. et al. "A Role for Autophosphorylation Revealed by Activated Alleles of *FUS3*, the Yeast MAP Kinase Homolog," *Molecular Biology of the Cell* 5:297-312 (1994).

(Continued)

*Primary Examiner*—James Ketter
*Assistant Examiner*—David A. Lambertson
(74) *Attorney, Agent, or Firm*—Edwards & Angell, LLP; Peter C. Lauro, Esq.

(57) ABSTRACT

The present invention makes available a rapid, reproducible, robust assay system for screening and identifying pharmaceutically effective compounds that specifically interact with and modulate the activity of a cellular protein, e.g., a receptor or ion channel. The subject assay enables rapid screening of large numbers of compounds to identify those which act as an agonist or antagonist to the bioactivity of the cellular protein. In particular, the assay of the invention makes use of a cell that harbors a protein that is responsive to a cellular signal transduction pathway. The protein is operatively linked to a polypeptide which causes a detectable signal to be generated upon stimulation of the pathway, e.g., when a compound interacts with and modulates the activity of a cellular receptor or ion channel of the cell. Thus, the cell provides a signal generation means comprising a novel fusion protein the expression of which is independent of stimulation/activation of the signal transduction pathway, but the activity of which is responsive to the signal transduction pathway.

49 Claims, No Drawings

OTHER PUBLICATIONS

Brugarolas, James et al. "Radiation-induced cell cycle arrest compromised by p21 deficiency," *Nature* 377:522-57 (1995).

Burack, W. Richard et al. "The Activating Dual Phosphorylation of MAPK by MEK Is Nonprocessive," *Biochemistry* 36(20):5929-5933 (1997).

Cavallini, Bruno et al. "A yeast activity can substitute for the HeLa Cell TATA box factor," *Nature* 334:77-80 (1988).

Chambers, D. A. et al. "Neuroimmune Modulation: Signal Transduction and Catecholamines," *Neurochem. Int.* 22(2): 95-110 (1993).

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1):11-20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999-1011 (1990).

Chien, Cheng-Ting, et al. "The two-hybrid system: A method to identify and clone genes for proteins that interact with a protein of interest," *Proc. Natl. Acad. Sci.* USA 88:9578-82 (1991).

Clark, Karen L. et al. "Interactions among the Subunits of the G-protein Involved in *Saccharomyces cerevisiae* Mating, " *Molecular and Cellular Biol.* 13(1):1-8 (1993).

Cole, Gary M. et al. "Stoichiometry of G Protein Subunits Affects the *Saccharomyces cerevisiae* Mating Pheromone Signal Transduction Pathway," *Molecular and Cellular Biology* 10(2):510-517 (1990).

Coleman, David E. et al. "Structures of Active Conformation of $G_{ia1}$ and the Mechanism of GTP Hydrolysis," *Science* 265:1405-12 (1994).

Conklin, Bruce R. et al. "Substitution of three amino acids switches receptor specificity of $G_{qa}$ to that $G_{ia1}$ " *Nature* 363:274-76 (1993).

Cwirla, Steven E. et al. "Peptides on phage: A vast library of peptides for identifying ligands," *Proc. Natl. Acad. Sci. USA* 87:6378-82 (1990).

Devlin, James J. et al. "Random Peptide Libraries: A Source of Specific Protein Binding Molecules," *Science* 249:404-6 (1990).

Dietzel, Christine and Kurjan, Janet "The Yeast SCG1 Gene: A Gα-like Protein Implicated in the a- and α-Factor Response Pathway," *Cell* 50:1001-10 (1987).

Dmochowska, Aleksandra et al. "Yeast *KEX1* Gene Encodes a Putative Protease with a Carboxypeptidase B-like Function Involved in Killer Toxin and α-Factor Precursor Processing, " *Cell* 50:573-84 (1987).

Dolan, J. W. et al. "Overproduction of the yeast STE12 protein leads to constitutive transcriptional induction," *Genes & Development* 4(4):492-502 (1990).

Dubois, Patrice M. et al. "Role of the transmembrane and cytoplasmic domains of surface IgM in endocytosis and signal transduction," *Eur. J. Immunol.* 22:851-57 (1992).

Erickson, Deborah "Intercepted Messages: New biotechnology drugs target intracellular communication," *Scientific American* 267(5):122-23 (1992).

Etienne, Gilles et al. "A Screening Method for Antifungal Substances Using *Saccharomyces cerevisiae* Strains Resistant to Polyene Macrolides," *J. of Antibiotics* 43(2): 199-206 (1990).

Fasullo, Michael T. and Davis, Ronald W. "Direction of Chromosome Rearrangements in *Saccharomyces cerevisiae* by Use of *his*3 Recombination Substrates," *Molecular and Cellular Biol.* 8(10):4370-80 (1988).

Ferrell, James E. Jr. "Tripping the switch fantastic: how a protein kinase cascade can convert graded inputs into switch-like outputs," *Trends in Biochem. Sci.* 21(12):460-6 (1996).

Ferrell, James E. Jr. et al. "The Biochemical Basis of an All-or-None Cell Fate Switch in *Xenopus Oocytes,* " *Science*280:895-898 (1998).

Fields, Stanley and Song Ok-kyu "A novel genetic system to detect protein-protein interactions," *Nature* 340:245-46 (1989).

Franke, Arthur E. et al. "Human C5a Anaphylatoxin: Gene Synthesis, Expression, and Recovery of Biologically Active Material from *Escherichia coli,"* Methods in Enzymology 162:653-68 (1988).

Funaro, Ana et al. "Human CD38 is associated to distinct molecules which mediate transmembrane signaling in different lineages," *Eur. J. Immunol.* 23:2407-11 (1993).

Gallego, Carme et al. "Mysristoylation of the $G_{ai2}$ polypeptide, a G protein α subunit, is required for its signaling and transformation functions," *Proc. Natl. Acad. Sci. USA* 89:9695-99 (1992).

Garritsen, Anja et al. "The N-Terminal coiled-coil domain of βis essential for γ association: A Model for G-Protein βγ subunit interaction," *Proc. Natl. Acad. Sci. USA* 90:7706-10 (1993).

Gerard, Norma P. and Gerard, Craig "Construction and Expression of a Novel Recombinant Anaphylatoxin, C5a-N19, a Probe for the Human C5a Receptor," *Biochemistry* 29(39):9274-81 (1990).

Gordon, J. "B-Cell signaling via the C-type lectins CD23 and CD72," *Immunology Today* 15(9):411-17 (1994).

Graf, Rolf et al. "A Truncated Recombinant α Subunit of $G_{i3}$ with a Reduced Affinity for βγ Dimers and Altered Guanosine 5'-3-O-(Thio)triphosphate Binding," *J. of Biol. Chem.* 267(34):24307-14 (1992).

Gros, Philippe et al. "Mammalian Multidrug Resistance Gene: Complete cDNA Sequence Indicates Strong Homology to Bacterial Transport Proteins," *Cell* 47:371-80 (1986).

Gyuris, Jenö et al. "Cdi1, A Human G1 and S Phase Protein Phosphatase That Associates with Cdk2," *Cell* 75:791-803 (1993).

Hagen, David C. et al. "Evidence the yeast *STE*3 gene encodes a receptor for the peptide pheromone a factor: Gene sequence and implications for the structure of the presumed receptor," *Proc. Natl. Acad. Sci. USA* 83:1418-22 (1986).

Hall, Marcia et al. "Evidence for different modes of action of cyclin-dependent kinase inhibitors: p15 and p16 bind to kinases, p21 and p27 bind to cyclins," *Oncogene* 11:1581-88 (1995).

Harbury, Pehr B. et al. "A Switch Between Two-, Three- and Four-Stranded Coiled Coils in GCN4 Leucine Zipper Mutants," *Science* 262:1401-07 (1993).

Hartwell, Leland H. "Mutants of *Saccharomyces cerevisiae* Unresponsive to Cell Division Control by Polypeptide Mating Hormone," *J. Cell Biol.* 85:811-22 (1980).

Hasson, M.S. et al. "Mutational Activation of the *STE*5 Gene Product Bypasses the Requirement for G Protein β and γ Subunits in the Yeast Pheromone Response Pathway," *Molecular and Cellular Biology* 14(2):1054-1065 (1994).

He, Bin et al. "*RAM2*, an essential gene of yeast, and *RAM*1 encode the two polyeptide components of the farnesyltransferase that prenylates a-actor and Ras proteins," *Proc. Natl. Acad. Sci. USA* 88:11373-77 (1991).

Hiltunen, J. Kalervo et al. "Peroxisomal Multifunctional β-Oxidation Protein of *Saccharomyces cerevisiae*," *J. of Biol. Chem.* 267(10):6646-6653 (1992).

Hrycyna, Christine A. et al. "The *Saccharomyces cerevisiae STE*14 gene encodes a methyltransferase that mediates C-terminal methylation of a-factor and RAS Proteins," *The EMBO J.* 10(1):1699-1709 (1991).

Huang, Chi-Ying F. et al. "Ultrasensitivity in the mitogen-activated protein kinase cascade," *Proc. Natl. Acad. Sci. USA* 93:10078-10083 (1996).

Hughes, David A. et al. "Complementation of *byr*1 in fission yeast by mammalian MAP kinase kinase requires coexpression of Raf kinase," *Nature* 364:349-52 (1993).

Imamoto, Akira et al. "Genetics of signal transduction: tales from the mouse," *Curr. Opin. Gen. & Dev.* 4:40-46 (1994).

Inouye, Carla et al. "Ste5 RING-H2 Domain: Role in Ste4-Promoted Oligomerization for Yeast Pheromone Signaling," *Science* 278:103-106 (1997).

Jabbar, M. Abdul et al. "Influenza Viral (A/WSN/33) hemagglutinin is expressed and glycosylated in the yeast *Saccharomyces cerevisiae*," *Proc. Natl. Acad. Sci. USA* 82:2019-23 (1985).

Jakobs, K. H. et al. "Dual regulation of adenylate cyclase. A signal transduction mechanism of membrane receptors," *Basic Res. Cardiol.* 81:1-9 (1986).

Journot, Laurent et al. "Amino Acids 367-376 of the $G_{i1}$ α subunit induce membrane association when fused to soluble amino-terminal deleted $G_{i1}$ a subunit," *Proc. Natl. Acad. Sci. USA* 88:10054-58 (1991).

Julius, David et al. "Yeast α Factor is Processed from a Larger Precursor Polypeptide: The Essential Role of a Membrane-Bound Dipeptidlyl Aminopeptidase," *Cell* 32:839-52 (1983).

Julius, David et al. "Glycosylation and Processing of Prepro-α-Factor through the Yeast Secretory Pathway," *Cell* 36:309-18 (1984).

Julius, David et al. "Isolation of the Putative Structural Gene for the Lysine-Arginine-Cleaving Endopeptidase Required for Processing of Yeast Prepro-α-factor," *Cell* 37:1075-89 (1984).

Kaiser, Chris A. et al. "Many Random Sequences Functionally Replace the Secretion Signal Sequence of Yeast Invertase," *Science* 235:312-17 (1987).

Kang, Yoon-Se et al. "Effects of expression of mammalian Gα and hybrid mammalian-yeast Gα proteins on the yeast pheromone response signal transduction pathway," *Molecular and Cellular Biology* 10(6):2582-250 (1990) *verify page numbers!!.*

King, Klim et al. "Control of Yeast Mating Signal Transduction by a Mammalian $β_2$-Adrenergic Receptor and $G_s$ α Subunit," *Science* 250:121-23 (1990).

Kingsman, S.M. et al. "*The production of mammalian protein in Saccharomyces cerevisiae*," *Tibtech* 5:53-57 (1987).

Koff, Andrew et al. "Human Cyclin E, a New Cyclin That Interacts with Two Members of the *CDC*2 Gene Family," *Cell* 66:1217-28 (1991).

Kosugi, Shinji et al. "Characterization of heterogeneous mutations causing constitutive activation of the luteinizing hormone receptor in familial male precocious puberty," *Human Molecular Genetics* 4(2):183-88 (1995).

Kramer, R. A. et al. "HTLV-III *gag* Protein is Processed in Yeast Cells by the Virus *pol*-Protease," *Science* 231:1580-85 (1986).

Kuchler, Karl et al. "*Saccharomyces cerevisiae* STE6 gene product: a novel pathway for protein export in eukaryotic cells," *The EMBO J.* 8(13):3973-84 (1989).

Kuchler, Karl and Thorner, Jeremy "Functional expression of human *mdr*1 in the yeast *Saccharomyces cerevisiae*," *Proc. Natl. Acad. Sci. USA* 89:2302-06 (1992).

Kurjan, Janet and Herskowitz "Structure of a Yeast Pheromone Gene (MFα): A Putative α-Factor Precursor Contains Four Random Copies of Mature α-Factor," *Cell* 30:933-43 (1982).

Kurjan, Janet "α-Factor Structural Gene Mutations in *Saccharomyces cerevisiae*: Effects on α-Factor Production and Mating," *Molecular and Cellular Biol.* 5(4):787-96 (1985).

Lambright, David G. et al. "Structural determinants for activation of the α-subunit of a heterotrimeric G protein," *Nature* 369:621-28 (1994).

Leberer, Ekkehard et al. "Dominant-negative mutants of a yeast G-protein β subunit identify two functional regions involved in pheromone signaling," *The EMBO J.* 11(13):4805-13 (1992).

Lee, Ethan et al. The G22A Mutant of $G_{sα}$Highlights the Requirement for Dissociation of G Protein Subunits, *J. Biol. Chem.* 267(2):1212-18 (1992).

Lemire, Bernard D. et al. "The Mitochondrial Targeting Function of Randomly Generated Peptide Sequence Correlates with Predicted Helical Amphiphilicity," *J. Biol. Chem.* 264(34):20206-12 (1989).

Lew, Daniel J. et al.. "Isolation of Three Novel Human Cyclins by Rescue of G1 Cyclin (Cin) Function in Yeast," *Cell* 66:1197-1206 (1991).

Linder, Maurine E. et al. "Lipid Modifications of G Protein Subunits: Myristoylation of $G_{Oα}$Increases its Affinity for βγ," *J. Biol. Chem.* 266(7):4654-59 (1991).

Linder, Maurine E. and Gilman, Alfred G. "G Proteins," *Scientific American* 267(1):56-65 (1992).

Lolait et al., "Extrapituitary expression of the rat V1b vasopressin receptor gene," *PNAS USA* 92:6783-6787 (1995).

Lupas, Andrei N. et al. "Do G protein subunits associate via a three-stranded coiled coil ?" *FEBS* 314(2):105-08 (1992).

Mackay, Vivian and Manney, Thomas R. "Mutations Affecting Sexual Conjugation and Related Processes in *Saccharomyces cerevisiae*. II Genetic Analysis of Nonmating Mutants," *Genetics* 76:273-88 (1974).

Marengere, Luc E.M. and Pawson, Tony "Structure and function of SH2 domains," *J. Cell Science Suppl.* 18:97-104 (1994).

Markby, David W. et al. "Separate GTP Binding and GTPase Activating Domains of a Gα Subunit," *Science* 262:1895-1901 (1993).

Michaelis, Susan and Herskowitz, Ira "The a-Factor Pheromone of *Saccharomyces cerevisiae* is Essential for Mating," *Molecular and Cellular Biol.* 8(3):1309-18 (1988).

Milano, C.A. et al. "Enhanced Myocardial Function in Transgenic Mice Overexpressing the $β_2$- Adrenergic Receptor," *Science* 264:582-86 (1994).

Milburn, Michael V. et al. "Molecular Switch for Signal Transduction: Structural Differences Between Active and Inactive Forms of Protooncogenic *ras* Proteins," *Science* 247:939-45 (1990).

Mumby, Susanne M. et al. "G-Protein α-subunit expression, myristoylation, and membrane association in COS cells," *Proc. Natl. Acad. Sci. USA* 87:728-32 (1990).

Murphy, A.J.M. et al. "Autocrine Stimulation of Yeast through Human G-Coupled Receptors," *J. Cell Biochem.* 18B:224 (1994).

Nakafuka, Masato et al. "Occurrence in *Saccharomyces cerevisiae* of a gene homologous to the cDNA coding for the α-subunit of mammalian G proteins," *Proc. Natl. Acad. Sci. USA* 84:2140-44 (1987).

Nakayama, N. et al. "Common signal transduction system shared by STE2 and STE3 in haploid cells of *Saccharomyces cerevisiae*: autocrine cell-cycle arrest results from forced expression of STE2," *The EMBO J.* 6(1):249-54 (1987).

Neer, Eva J. et al. "The Amino Terminus of a G Protein α Subunits Is Required for Interaction with βγ," *J. Biol. Chem.* 263(18):8996-9000 (1988).

Noel, Joseph P. et al. "The 2.2 Å crystal structure of transducin-α complexed with GTP-γ-S," *Nature* 366:654-63 (1993).

Noelle, Randolph J. et al. "CD40 and its ligand, an essential ligand-receptor pair for thymus- dependent B-cell activation," *Immunol. Today* 13(11):431-33 (1992).

Nomoto, Satoshi et al. "Regulation of the yeast pheromone response pathway by G protein subunits," *The EMBO J.* 9(3):691-696 (1990).

Nye, Jeffrey S. and Kopan, Raphael "Vertebrate ligands for Notch," *Current Biology* 5(9):966-69 (1995).

Oeda, Kenji et al. "Expression of Rat Liver Cytochrome P-450MC cDNA in *Saccharomyces cerevisiae*," *DNA* 4(3):203-10 (1985).

Ogden, Jill E. et al. "Efficient Expression of the *Saccharomyces cerevisiae* PGK Gene Depends on an Upstream Activation Sequence but Does Not Require TATA Sequences," *Molecular and Cellular Biol.* 6(12):4335-43 (1986).

Pronin, Alexey N. and Gautam, Narasimhan "Interaction between G-Protein β and γ subunit types is selective," *Proc. Natl. Acad. Sci. USA* 89:6220-24 (1992).

Ramer, Sandra W. and Davis, Ronald W. "A dominant truncation allele identifies a gene, *STE20*, that encodes a putative protein kinase necessary for mating in *Saccharomyces cerevisiae*," *Proc. Natl. Acad. Sci. USA* 90:452-456 (1993).

Ranade, Koustubh et al. "Mutations associated with familial melanoma impair p16$^{INK4}$ function," *Nature Genetics* 10:114-16 (1995).

Rarick, Helen M. et al. "A Site on Rod G Protein α Subunit That Mediates Effector Activation," *Science* 256:1031-33 (1992).

Raymond, Martine et al. "Functional Complemetation of Yeast *ste6* by a Mammalian Multidrug Resistence *mdr* Gene," *Science* 256:232-34 (1992).

Reed, Randall R. "G Protein Diversity and the Regulation of Signaling Pathways," *The New Biologist* 2(11):957-60 (1990).

Schafer, William R. et al. "Genetic and Pharmacological Suppression of Oncogenic Mutations in *RAS* Genes of Yeast and Humans," *Science* 245:379-85 (1989).

Schafer, William R. et al. "Enzymatic Coupling of Cholesterol Intermediates to a Mating Pheromone Precursor and to the Ras Protein," *Science* 249:1133-39 (1990).

Schärer, E. and Iggo, R. "Mammalian p53 can function as a transcription factor in yeast," *Nucleic Acids Research* 20(7):1539-45 (1992).

Scott, Jamie K. and Smith, George P. "Searching for Peptide Ligands with an Epitope Library," *Science* 249:386-90 (1990).

Sikorski, Robert S. and Hieter, Philip "A System of Shutte Vectors and Yeast Host Strains Designed for Efficient Manipulation of DNA in *Saccharomyces cerevisiae*," *Genetics* 122:19-27 (1989).

Singh, Arjun et al. "*Saccharomyces cerevisiae* contains two discrete genes coding for the α-factor pheromone," *Nucleic Acids Research* 11(12):4049-63 (1983).

Slepak, Vladlen Z. et al. "Mutational Analysis of G Protein α Subunit $G_{o\alpha}$Expressed in *Escherichia coli*," *J. Biol. Chem.* 268(2):1414-23 (1993).

Spiegel, Allen M. et al. "The G Protein connection: molecular basis of membrane association," *TIBS* 16:338-41 (1991).

Steube, Klaus et al. "α-Factor-leader-directed secretion of recombinant human-insulin-like growth factor I from *Saccharomyces cerevisiae*," *Eur. J. Biochem.* 198:651-57 (1991).

Stevenson, Brian J. et al. "Constitutive mutants of the Protein Kinase STE11 Activate the Yeast Pheromone Response Pathway in the Absence of the G Protein," *Genes & Development* 6:1293-1304 (1992).

Strubin, Michel and Struhl, Kevin "Yeast and Human TFIID with Altered DNA-Binding Specificity of TATA Elements," *Cell* 68:721-30 (1992).

Struhl, Kevin et al. "High-Frequency transformation of yeast: Autonomous replication of hybrid DNA molecules," *Proc. Natl. Acad. Sci. USA* 76(3):1035-39 (1979).

Struhl, Kevin "Constitutive and Inducible *Saccharomyces cerevisiae* Promoters: Evidence for Two Distinct Molecular Mechanisms," *Molecular and Cellular Biol.* 6(11):3847-53 (1986).

Struhl, Kevin and Hill, David E. "Two Related Regulatory Sequences are Required for Maximal Induction of *Saccharomyces cerevisiae his*3 Transcription," *Molecular and Cellular Biol.* 7(1):104-10 (1987).

Sullivan, Kathleen A. et al., "Identification of receptor contact site involved in receptor-G protein coupling," *Nature* 330:758-60 (1987).

Suzuki, Takeshi et al. "HTLV-1 Tax protein interacts with cyclin-dependent kinase inhibitor p16$^{INK4A}$ and counteracts its inhibitory activity towards CDK4," *The EMBO J.* 15(7):1607-14 (1996).

Teem, John L. et al. "Identification of Revertants for the Cystic Fibrosis ΔF508 Mutation Using STE6-CFTR Chimeras in Yeast," *Cell* 73:335-346 (1993).

Thomas, Thomas C. et al. "G-protein $\alpha_o$ subunit: Mutation of conserved cysteines identifies a subunit contact surface and alters GDP affinity," *Proc. Natl. Acad. Sci. USA* 90:10295-99 (1993).

Tyson, John J. et al. "Chemical kinetic theory: understanding cell-cycle regulation," *Trends in Biochem. Sci.* 21:89-96 (1996).

Walker, John E. et al. "Distantly related sequences in the α-and β-subunits of ATP synthase, myosin, kinases and other ATP-requiring enzymes and a common nucleotide binding fold," *The EMBO J.* 1(8):945-51 (1982).

Waters, M. Gerard et al. "Prepro-α-factor Has a Cleavable Signal Sequence," *J. Biol. Chem.* 263(13):6209-14 (1988).

Whiteway, Malcolm et al. "The *STE4* and *STE18* Genes of Yeast Encode Potential β and γ Subunits of the Mating Factor Receptor-Coupled G Protein," *Cell* 56:467-477 (1989).

Whiteway, Malcolm et al. "Dominant negative selection of heterologous genes: Isolation of *Candida albicans* genes that interfere with *Saccharomyces cerevisiae* mating factor-induced cell cycle arrest," *Proc. Natl. Acad. Sci. USA* 89:9410-14 (1992).

Whiteway, Malcolm et al. "Genetic Identification of Residues Involved in Association of α and β G-Protein Subunits," *Molecular and Cellular Biol.* 14(5):3223-3229 (1994).

Whiteway, Malcolm S. et al. "Association of the Yeast Pheromone Response G Protein βγ Subunits with the MAP Kinase Scaffold Ste5p," *Science* 269:1572-1575 (1995).

Wolowiec, D. et al. "Expression of cell cycle regulatory proteins in chronic lymphocytic leukemias. Comparison with non-Hodgkin's lymphomas and non-neoplastic lymphoid tissue," *Leukemia* 9:1382-88 (1995).

Xiong, Yue et al. "Human D-Type Cyclin," *Cell* 65:691-99 (1991).

Xiong, Yue et al. "Alteration of Cell Cycle Kinase Complexes in Human Papillomavirus E6- and E7- Expressing Fibroblasts Precedes Neoplastic Transformation," *J. Virology* 70(2):999-1008 (1996).

Zervos, Antonis S. et al. "Mxi1, a Protein that Specifically Interacts with Max to Bind Myc-Max Recognition Sites" *Cell* 72:223-32 (1993).

Zhan, Xiao-Li et al. "Differential regulation of *FUS*3 MAP kinase by tyrosine-specific phosphatases *PTP*2/*PTP*3 and dual-specificity phosphatase *MSG*5 in *Saccharomyces cerevisiae*," *Genes & Development* 11:1690-1702 (1997).

Dietzel et al. Pheromonal regulation and sequence of the *Saccharomyces cerevisiae* SST2 gene: a model desensitization to pheromone. Mol. Cell. Biol. 7:4169-4177.

Pi et al. Transcriptional activation upon pheromone stimulation mediated by a small domain of *Saccharomyces cerevisiae* Ste 12p. Mol. Cell. Biol. 17:6410-6418.

SEQUENCE LISTING

```
<160> NUMBER OF SEQ ID NOS: 5

<210> SEQ ID NO 1
<211> LENGTH: 31
<212> TYPE: DNA
<213> ORGANISM: synthetic construct

<400> SEQUENCE: 1 ctaggatcc gggagaggca taatctggca c                                   31

<210> SEQ ID NO 2
<211> LENGTH: 37
<212> TYPE: DNA
<213> ORGANISM: synthetic construct

<400> SEQUENCE: 2
gatcgaattc ggtatcaata aagatatcga ggagtgc                            37

<210> SEQ ID NO 3
<211> LENGTH: 39
<212> TYPE: DNA
<213> ORGANISM: synthetic construct

<400> SEQUENCE: 3
gatcggatcc atgccaaaga gaattgtata caatatatc                          39

<210> SEQ ID NO 4
<211> LENGTH: 40
<212> TYPE: DNA
<213> ORGANISM: synthetic construct

<400> SEQUENCE: 4
acgcgtcgac taactaaata tttcgttcca aatgagtttc                         40

<210> SEQ ID NO 5
<211> LENGTH: 31
<212> TYPE: DNA
<213> ORGANISM: synthetic construct
<220> FEATURE:
<223> OTHER INFORMATION: At positions 6 and 12, W is A or T
<220> FEATURE:
<223> OTHER INFORMATION: At position 7, M is A or C

<400> SEQUENCE: 5
ccacawmttc cwccatgccg ctttgctgac c                                  31
```

CELL BASED SIGNAL GENERATION

This application is a continuation of U.S. application Ser. No. 09/241,888, filed Feb. 1, 1999, now issued as U.S. Pat. No. 6,504,008.

BACKGROUND OF THE INVENTION

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints have been exploited in cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase, inasmuch as the use of whole animals is labor-intensive and extremely expensive.

The search for agonists and antagonists of cellular receptors has been an intense area of research aimed at drug discovery because of the elegant specificity of these molecular targets. Drug screening has been carried out using whole cells expressing functional receptors and, recently, binding assays employing membrane fractions or purified receptors have been designed to screen compound libraries for competitive ligands.

The heterologous expression of recombinant mammalian G protein-coupled receptors in mammalian cells which do not normally express those receptors has been described as a means of studying receptor function for the purpose of identifying agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidylinositol hydrolysis and intracellular $Ca^{2+}$ mobilization in Chinese hamster ovary cells upon agonist stimulation (Lolait et al. (1995) *Proc. Natl. Acad Sci.* USA 92:6783–6787). These types of ectopic expression studies have enabled researchers to study receptor signaling mechanisms and to perform mutagenesis studies which have been useful in identifying portions of receptors that are critical for ligand binding or signal transduction.

Experiments have also been undertaken to express functional G protein-coupled receptors in yeast cells. For example, U.S. Pat. No. 5,482,835 to King et al. describes a transformed yeast cell which is incapable of producing a yeast G protein α subunit, but which has been engineered to produce both a mammalian G protein α-subunit and a mammalian receptor which is "coupled to" (ie., interacts with) the aforementioned mammalian G protein α-subunit. Specifically, U.S. Pat. No. 5,482,835 reports expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast α-factor receptor.) It was found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 also describes co-expression of a rat G protein α-subunit in yeast strain 8C, which lacks the cognate yeast protein. Ligand binding resulted in G protein-mediated signal transduction. U.S. Pat. No. 5,482,835 further teaches that these cells may be used in screening compounds for the ability to affect the rate of dissociation of Gα from Gβγ in a cell. For this purpose, the cell further contains a pheromone-responsive promoter (e.g., BAR1 or FUS1), linked to an indicator gene (e.g. HIS3 or lacZ). The cells are placed in multi-titer plates, and different compounds are placed in each well. The colonies are then scored for expression of the indicator gene.

U.S. Pat. No. 5,789,184 describes yeast cells engineered to express a heterologous kinase as a yeast pheromone system protein surrogate, and a heterologous polypeptide. The yeast cells are used in assays to screen for peptides that modulate the activity of non-yeast surrogates.

Published PCT international application WO 98/13513 describes methods for identifying modulators of heterologous receptors expressed in yeast. Modulators are identified by detecting an alteration in a signal produced by an endogenous yeast signaling pathway.

U.S. Pat. No. 4,833,080 discloses regulation of eukaryotic gene expression using a two component chimeric fusion protein. The chimeric fusion protein consists of a DNA binding domain and a transcriptional activation domain.

SUMMARY OF THE INVENTION

The present invention relates to a novel, rapid, reproducible, robust assay system for screening and identifying pharmaceutically effective compounds that specifically interact with and modulate the activity of a cellular receptor or ion channel of a cell.

The assay of the invention makes use of a cell that harbors a protein that is responsive to a cellular signal transduction pathway. The protein is operatively linked to a polypeptide which causes a detectable signal to be generated upon stimulation of the pathway, e.g., when a compound interacts with and modulates the activity of a cellular receptor or ion channel of the cell. Thus, the cell provides a signal generation means comprising a novel fusion protein the expression of which is independent of stimulation/activation of the signal transduction pathway, but the activity of which is responsive to the signal transduction pathway.

The present invention provides for the use of any type of cell in the subject assays, whether prokaryotic or eukaryotic. In preferred embodiments, the cells of the present invention are eukaryotic. In certain preferred embodiments the cells are mammalian cells. In other preferred embodiments the cells are yeast cells, with cells from the genera *Saccharomyces* or *Schizosaccharomyces* being more preferred. The host cells can be derived from primary cells, or from transformed and/or immortalized cell lines.

The subject assays provide a means for detecting the ability of compounds to modulate the signal transduction activity of the target receptor by scoring for up- or down-regulation of a detection signal. Signal transduction can be measured in a variety of ways, including but not limited to, physical and biological methods, enzymatic methods, and transcriptional activation of endogenous genes or reporter genes. For example, endogenous yeast second messenger generation (e.g., GTP hydrolysis, calcium mobilization, or phospholipid hydrolysis) or increased transcription of an endogenous gene can be detected directly. Alternatively, the use of a reporter or indicator gene can provide a convenient readout. By whatever means measured, a change (e.g., a statistically significant change) in the detection signal can be used to facilitate isolation of those cells from the mixture which have received a signal via the target receptor, and thus can be used to identify novel compounds which function as receptor agonists or antagonists.

In one embodiment of the present invention, the reagent cells express the receptor of interest endogenously. In other embodiments, the cells are engineered to express a heterologous receptor protein. In either of these embodiments, it may be desirable to inactivate one or more endogenous genes of the host cells. For example, certain preferred embodiments in which a heterologous receptor is provided utilize host cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein coupled receptor. Other complementations include, for example, expression of heterologous MAP kinases or erk kinases, MEKs or MKKs (MAP kinase kinases), MEKKs (MEK kinases), PAKs (p21-activated kinases, e.g., Ste 20), ras and the like.

In one embodiment, the assay of the present invention can be used to screen compounds, e.g., small molecules, which are exogenously added to cells in order to identify potential receptor effector compounds. In another embodiment the subject assays enable rapid screening of large numbers of polypeptides in a library expressed in the cell in order to identify those polypeptides which agonize or antagonize receptor bioactivity, creating an autocrine system. The autocrine assay is characterized by the use of a library of recombinant cells, each cell of which includes a target receptor protein whose signal transduction activity can be modulated by interaction with an extracellular signal, the transduction activity being able to generate a detectable signal, and an expressible recombinant gene encoding an exogenous test polypeptide from a polypeptide library. By the use of a gene library, the mixture of cells collectively expresses a population of test polypeptides. In preferred embodiments, the polypeptide library includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another embodiment of the assay, if a test compound does not appear to directly induce the activity of the receptor protein, the assay may be repeated and modified by the introduction of a step in which the cell is first contacted with a known activator of the target receptor to induce the signal transduction pathways from the receptor. Thus, a test compound can be assayed for its ability to antagonize, e.g., inhibit or block the activity of the activator. Alternatively, the assay can score for compounds which potentiate the induction response generated by treatment of the cell with a known activator.

A particularly advantageous feature of the invention is a recombinant yeast cell that harbors a yeast protein that is sensitive/responsive to a signaling pathway of the yeast cell, and that is operatively linked to a polypeptide, such that the polypeptide causes a detectable signal to be generated when the pathway is stimulated.

Accordingly, in one aspect, the invention features a recombinant yeast cell comprising a yeast protein operatively linked to a polypeptide, wherein the yeast protein is responsive to a signal transduction pathway of the cell, and the activity of the yeast protein is modulated directly or indirectly upon stimulation of the pathway, and wherein upon modulation of the yeast protein, the polypeptide causes a detectable signal to be generated.

In one embodiment, the signal transduction pathway is a yeast pheromone response pathway.

In another embodiment, the recombinant yeast cell further comprises a gene which produces a detectable protein. In a preferred embodiment, the gene that produces the detectable protein is selected from the group consisting of ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ, LEU1, LEU2, LEU4, luciferase, LYS2, MAL, MEL, MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10. In another preferred embodiment, the gene is selected from the group consisting of CAT, GAL1, GAL7, GAL10, GFP, HIS3, lacZ, luciferase, LEU2, MEL, PHO5, and URA3. In yet another embodiment, the gene is an endogenous gene at its natural location in the yeast cell, and the polypeptide causes the endogenous yeast gene to produce the detectable protein. In a preferred embodiment, the natural location in the yeast cell is the natural location of the endogenous gene in the yeast genome.

In one embodiment, the detectable protein is selected from the group consisting of α-galactosidase, β-galactosidase, alkaline phosphatase, horseradish peroxidase, exoglucanase, luciferase, Bar1, Pho5 acid phosphatase, green fluorescent protein, chitinase, and chloramphenicol acetyl transferase. In a preferred embodiment, the detectable protein is β-galactosidase.

In another embodiment, the recombinant yeast cell further comprises a heterologous receptor that is functionally integrated into the signal transduction pathway. In a preferred embodiment, the heterologous receptor is expressed in the cell membrane of the yeast cell. In another preferred embodiment, the heterologous receptor is selected from the group consisting of melatonin receptor 1a, galanin receptor 1, neurotensin receptor, adenosine receptor 2a, somatostatin receptor 2, and corticotropin releasing factor receptor 1. In yet another preferred embodiment, the heterologous receptor is melatonin receptor 1a.

In one embodiment, the activity of the yeast protein is directly modulated upon stimulation of the signal transduction pathway. In a preferred embodiment, the yeast protein is a wild type yeast protein.

In another embodiment, the activity of the yeast protein is indirectly modulated upon stimulation of the signal transduction pathway. In a preferred embodiment, the yeast protein is a mutant yeast protein, the activity of which is modulated by a wild type yeast protein, and wherein the activity of the wild type yeast protein is directly modulated upon stimulation of the signal transduction pathway. In another preferred embodiment, the mutant yeast protein is derived from the wild type yeast protein.

In one embodiment, the yeast protein is selected from the group consisting of Fus3, Hog1, Kss1, Mpk1, Smk1, Bem1, Cdc24, Cdc42, Dig1, Dig2, Far1, Gpa1, Msg5, Ste4, Ste5, Ste7, Ste11, Ste12, Ste18, Ste20 and Sst2. In preferred embodiments, the yeast protein is Fus3, Hog1, Kss1, Far1, Ste5 and Ste11.

In one embodiment, the polypeptide is a transcription factor. The transcription factor is selected from the group consisting of bacterial, viral and eukaryotic transcription factors. In a preferred embodiment, the transcription factor is a yeast transcription factor. The yeast transcription is selected from the group consisting of Ste12, Gal4, Pho4, Gcn4, Hap1, Adr1, Ace2, Cup2, Swi5 and Bas1. In preferred embodiments, the yeast transcription factor is Ste12, Gal4, and Pho4.

In another embodiment, the polypeptide is a chimeric transcription factor comprising a DNA binding domain (DBD) operatively linked to a transcriptional activation domain (AD). In one embodiment, the DNA binding domain and transcriptional activation domain are derived from the same protein. In another embodiment, the DNA binding domain and transcriptional activation domain are derived from different proteins. In a preferred embodiment, the DNA binding domain comprises a polypeptide sequence derived from a polypeptide selected from the group consisting of LexA, Gal4, Adr1, Ace2, Cup2, Bas1, Gcn4, Swi5, Pho4, Hap1 and LacI, and the transcriptional activation domain comprises a polypeptide sequence derived from a polypeptide selected from the group consisting of B42, Gal4, Adr1, Ace2, Cup2, Bas1, Gcn4, Swi5, Pho4, Hap1, VP16, and Ste12.

In preferred embodiments, the DNA binding domain comprises a polypeptide sequence derived from LexA, from Gal4, and from Pho4. In other preferred embodiments, the transcriptional activation domain comprises a polypeptide sequence derived from B42, from VP16, from Gal4, or from Ste12.

In particularly preferred embodiments, the chimeric transcription factor comprises: a LexA DNA binding domain operatively linked to a B42 transcriptional activation domain; a Gal4 DNA binding domain operatively linked to a B42 transcriptional activation domain; a Gal4 DNA binding domain operatively linked to a VP16 transcriptional activation domain; and a Gal4 DNA binding domain operatively linked to a Gal4 transcriptional activation domain II.

In one embodiment, the recombinant yeast cell further comprises a promoter, wherein transcription of the gene that produces the detectable protein is controlled by the promoter. Upon modulation of the activity of the yeast protein, the transcription factor activates transcription of the gene that produces the detectable protein. In a preferred embodiment, the promoter is selected from the group consisting of Gal1, Gal10, Mel and LexA operator. In another embodiment, the promoter is operatively linked to an endogenous gene in its natural location in the yeast cell.

In another embodiment, the polypeptide comprises a protein that can be an enzyme, a protein required for cell viability, or an indicator molecule. The protein is selected from the group consisting of Ade1, Ade2, Ade3, Ade4, Ade5, Ade7, Ade8, Asp3, Arg1, Arg3, Arg4, Arg5, Arg6, Arg8, Aro2, Aro7, Bar1, CAT, Cho1, Cys3, Gal1, Gal7, Gal10, GFP, His1, His3, His4, His5, Hom3, Hom6, Ilv1, Ilv2, Ilv5, Ino1, Ino2, Ino4, lacZ, Leu1, Leu2, Leu4, luciferase, Lys2, Mal, Mel, Met2, Met3, Met4, Met8, Met9, Met14, Met16, Met19, Ole1, Pho5, Pro1, Pro3, Thr1, Thr4, Trp1, Trp2, Trp3, Trp4, Trp5, Ura1, Ura2, Ura3, Ura4, Ura5, Ura10, Cdc25, Cyr1 and Ras, or fragment thereof. In a preferred embodiment, the polypeptide is an enzyme. In another preferred embodiment, the enzyme is selected from the group consisting of CAT, Gal1, lacZ, Mel, and Pho5. In another preferred embodiment, the protein is a protein required for cell viability. In yet another preferred embodiment, the protein required for cell viability is selected from the group consisting of Gal1, His3, Leu2, Mel, Ura3, Cdc25, Cyr1 and Ras. In another embodiment, the polypeptide is an indicator molecule. In a preferred embodiment, the indicator molecule is GFP.

In another embodiment, the yeast cell further comprises a heterologous test polypeptide, wherein the heterologous test polypeptide is transported to a location allowing interaction with the extracellular region of the heterologous receptor, and wherein the heterologous test polypeptide is expressed at a sufficient level such that modulation of the signal transduction activity of the receptor by the heterologous test polypeptide alters the detectable signal. In a preferred embodiment, the heterologous test polypeptide includes a signal sequence that facilitates transport of the polypeptide to a location allowing interaction with the extracellular region of the receptor.

In another aspect, the invention features a recombinant yeast cell as herein above described, except that a pheromone responsive yeast protein is operatively linked to a chimeric transcription factor such that the chimeric transcription factor causes a detectable signal to be generated upon stimulation of a yeast pheromone response pathway. Thus, the invention is directed to a recombinant yeast cell comprising a yeast protein operatively linked to a chimeric transcription factor, and a gene which produces a detectable protein, wherein the yeast protein is responsive to a yeast pheromone response pathway, and the activity of the yeast protein is modulated directly or indirectly upon stimulation of the pathway of the yeast cell, and wherein upon modulation of the yeast protein, the chimeric transcription factor causes a detectable signal to be generated.

In one embodiment, the yeast cell further comprises a heterologous receptor that is functionally integrated into the yeast pheromone response pathway. In a preferred embodiment, the heterologous receptor is selected from the group consisting of melatonin receptor 1a, galanin receptor 1, neurotensin receptor, adenosine receptor 2a, somatostatin receptor 2, and corticotropin releasing factor receptor 1. In another preferred embodiment, the heterologous receptor is melatonin receptor 1a.

In a preferred embodiment, the yeast protein is wild type Fus3. In another preferred embodiment, the yeast protein is mutated Fus3. The mutated Fus3 may comprise an amino acid substitution at positions 42, 180 or 182, or at positions 180 and 182, of the wild type Fus3 amino acid sequence. Preferred substitutions at position 42 include arginine; at position 180, valine and glutamic acid; and at position 182, asparagine and valine. Preferred amino acid substitutions in the wild Fus3 yeast protein are Lys42Arg, Thr180Val, Thr180Glu, Try182Val, and Try182Asp.

In another preferred embodiment, the chimeric transcription factor comprises: a LexA DNA binding domain operatively linked to a B42 transcriptional activation domain; a Gal4 DNA binding domain operatively linked to a B42 transcriptional activation domain; a Gal4 DNA binding domain operatively linked to a VP16 transcriptional activation domain; and a Gal4 DNA binding domain operatively linked to a Gal4 transcriptional activation domain II.

In yet another embodiment, the recombinant yeast cell further comprises a promoter operatively linked to the gene, such that upon modulation of the activity of the yeast protein that is responsive to the yeast pheromone response pathway of the cell, the activity of the chimeric transcription factor is stimulated, thereby activating transcription of the gene that produces the detectable protein. In a preferred embodiment, the promoter comprises the minimal Gal promoter and LexA operators, the gene is the lacZ gene, and the detectable protein is β-galactosidase.

In another aspect, the invention features methods that use the recombinant yeast cells herein above described to identify compounds that modulate a receptor expressed by the recombinant yeast cells. Thus, the invention is directed to a method for identifying a test compound that modulates a receptor expressed by a recombinant yeast cell comprising:

providing a recombinant yeast cell that expresses the receptor which is functionally integrated into a signal transduction pathway of the yeast cell, wherein the yeast cell comprises a yeast protein which is responsive to the signal transduction pathway and which is operatively linked to a polypeptide, and wherein the activity of said yeast protein is modulated directly or indirectly upon stimulation of the pathway, and wherein upon modulation of the yeast protein, the polypeptide causes a detectable signal to be generated;

contacting the yeast cell with a test compound; and detecting an alteration in the signal to thereby identify a compound that modulates the receptor.

The invention is also directed to a method for identifying a test compound that modulates a receptor expressed by a recombinant yeast cell comprising:

providing a recombinant yeast cell that expresses a receptor which is functionally integrated into a yeast pheromone response pathway, wherein the yeast cell comprises a yeast protein which is responsive to the pheromone response pathway and which is operatively linked to a chimeric transcription factor, and a gene which produces a detectable protein, and wherein the activity of the yeast protein is modulated directly or indirectly upon stimulation of the pathway, and wherein upon modulation of the yeast protein, the chimeric transcription factor causes a detectable signal to be generated;

contacting the yeast cell with a test compound; and detecting an alteration in the signal to thereby identify a compound that modulates the receptor.

In one embodiment of the methods of the invention, the test compound is derived from a peptide library. In another embodiment, the test compound is derived from a library of non-peptidic compounds. In yet another embodiment, the test compound is derived from a library of test polypeptides expressed by the cell.

In one embodiment, the step of detecting the alteration in the signal comprises measuring the transcription of an endogenous gene or the activity of an endogenous protein in the cell.

In another aspect, the invention features a chimeric nucleic acid construct comprising:

a first segment comprising a nucleotide sequence encoding a yeast protein or fragment thereof which is responsive to a signal transduction pathway of a yeast cell, wherein the activity of the yeast protein or fragment thereof is modulated directly or indirectly upon stimulation of a the signal transduction pathway; and a second segment comprising a nucleotide sequence encoding a polypeptide that causes a detectable signal to be generated upon modulation of the yeast protein.

In one embodiment, the signal transduction pathway is a yeast pheromone pathway. In another embodiment, the first segment encodes a yeast protein selected from the group consisting of Fus3, Hog1, Kss1, Mpk1, Smk1, Bem1, Cdc24, Cdc42, Dig1, Dig2, Far1, Gpa1, Msg5, Ste4, Ste5, Ste7, Ste11, Ste12, Ste18, Ste20 and Sst2. In preferred embodiments, the first segment encodes Fus3, Far1, Ste5, Ste11, and Ste12.

In one embodiment, the second segment encodes a polypeptide comprising a transcription factor. In a preferred embodiment, the second segment encodes a polypeptide selected from the group of yeast transcription factors. These include, but are not limited to, Ste12, Gal4, Pho4, Gcn4, Hap1, Adr1, Ace2, Cup2, Swi5 and Bas1.

In another embodiment, the second segment encodes a chimeric transcription factor. The second segment comprises a third segment comprising a nucleotide sequence encoding a DNA binding domain, and a fourth segment comprising a nucleotide sequence encoding a transcriptional activation domain. In one embodiment, the third and fourth segments are derived from the same gene. In another embodiment, the third and fourth segments are derived from different genes. In preferred embodiments, the third segment encodes a polypeptide comprising: LexA DNA binding domain; or a Gal4 DNA binding domain. In other preferred embodiments, the fourth segment encodes a polypeptide comprising: a B42 transcriptional activation domain; or a Gal4 transcriptional activation domain II.

In another embodiment, the second segment encodes a polypeptide comprising a protein that can be an enzyme, a protein required for cell viability, or an indicator molecule. The protein is selected from the group consisting of Ade1, Ade2, Ade3, Ade4, Ade5, Ade7, Ade8, Asp3, Arg1, Arg3, Arg4, Arg5, Arg6, Arg8, Aro2, Aro7, Bar1, CAT, Cho1, Cys3, Gal1, Gal7, Gal10, GFP, His1, His3, His4, His5, Hom3, Hom6, Ilv1, Ilv2, Ilv5, Ino1, Ino2, Ino4, lacZ, Leu1, Leu2, Leu4, luciferase, Lys2, Mal, Mel, Met2, Met3, Met4, Met8, Met9, Met14, Met16, Met19, Ole1, Pho5, Pro1, Pro3, Thr1, Thr4, Trp1, Trp2, Trp3, Trp4, Trp5, Ura1, Ura2, Ura3, Ura4, Ura5, Ura10, Cdc25, Cyr1 and Ras, or fragment thereof In a preferred embodiment, the polypeptide is an enzyme. In another preferred embodiment, the enzyme is selected from the group consisting of CAT, Gal1, lacZ, Mel, and Pho5. In another preferred embodiment, the protein is a protein required for cell viability. In yet another preferred embodiment, the protein required for cell viability is selected from the group consisting of Gal1, His3, Leu2, Mel, Ura3, Cdc25, Cyr1 and Ras. In another embodiment, the protein is an indicator molecule. In a preferred embodiment, the indicator molecule is GFP.

In another aspect, the invention features fusion proteins encoded by the chimeric nucleic acid constructs herein above described.

In one embodiment, the invention is directed to a fusion protein comprising a yeast protein responsive to a signal transduction pathway of a yeast cell operatively linked to a protein that is an enzyme, a protein required for cell viability, or an indicator molecule. In a preferred embodiment, the fusion protein comprises Ste5 operatively linked to Ras. In another preferred embodiment, the fusion protein comprises Ste11 operatively linked to His3.

In another embodiment, the invention is directed to a fusion protein comprising a yeast protein responsive to a signal transduction pathway of a yeast cell operatively linked to a chimeric transcription which comprises a DNA binding domain operatively linked to a transcriptional activation domain. In a preferred embodiments, the fusion protein comprises: a polypeptide selected from the group consisting of a LexA DNA binding domain operatively linked to a B42 transcriptional activation domain operatively linked to Fus3; a Gal4 DNA binding domain operatively linked to a B42 transcriptional activation domain operatively linked to Fus3; and a Gal4 DNA binding domain operatively linked to a Gal4 transcriptional activation domain II operatively linked to Fus3.

DETAILED DESCRIPTION OF THE INVENTION

Proliferation, differentiation and death of eukaryotic cells are controlled by a variety of extracellular signals, such as hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds.

The present invention makes available a rapid, effective assay for screening and identifying pharmaceutically effective compounds that specifically interact with and modulate the activity of a cellular receptor, ion channel, or a surrogate of a pheromone response pathway component. The subject assay enables rapid screening of large numbers of compounds including, for example, small organic molecules, or polypeptides in an expression library to identify compounds which induce or antagonize receptor bioactivity.

A particularly advantageous feature of the assay is a novel fusion protein which comprises a protein which is responsive/sensitive to activation of a cellular signal transduction pathway, and which is operatively linked to a polypeptide. By virtue of its operative linkage to the protein, the polypeptide causes a detectable signal to be generated upon stimulation/activation of the cellular signal transduction pathway. Expression of the fusion protein of the invention is independent of stimulation/activation of the signal transduction pathway. However, the activity of the fusion protein is signal transduction-responsive because it comprises a signal transduction-responsive protein the activation of which is modulated directly or indirectly by stimulation of pathway. Thus, the novel fusion protein of the invention confers signal transduction responsiveness on cellular moieties (e.g., transcriptional regulatory elements, enzymes, etc.) that are not naturally responsive to activation of that signal transduction pathway.

The assay of the present invention provides a convenient format for discovering drugs which can be useful to modulate cellular function, as well as to understand the pharmacology of compounds that specifically interact with cellular receptors, ion channels, and components that modulate a surrogate of the pheromone response pathway, e.g., kinases, farnesyltransferases, and ABC transporters. Moreover, the subject assay is particularly amenable to identifying ligands, natural or artificial, for receptors and ion channels.

I. Definitions

Before further description of the invention, certain terms employed in the specification, examples and appended claims are, for convenience, collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a reporter gene construct, heterologous receptor or test polypeptide.

The term "yeast protein" as used herein refers to a protein that is sensitive/responsive to, and modulated by a yeast signal transduction pathway. The yeast protein is operatively linked to a polypeptide. The term "yeast protein" is intended to include a full length protein, or a fragment thereof, that is sensitive/responsive to the yeast signal transduction pathway.

The terms "operatively linked", "operably linked", and "associated with" are used herein interchangeably and are intended to mean that molecules are functionally coupled to each other in that the change of activity or state of one molecule is affected by the activity or state of the other molecule. Typically, two polypeptides are covalently attached through peptide bonds.

The terms "protein", and "polypeptide" are used interchangeably herein. The term "peptide" is used herein to refer to a chain of two or more amino acids or amino acid analogs (including non-naturally occurring amino acids), with adjacent amino acids joined by peptide (—NHCO—) bonds. Thus, the peptides of the invention include oligopeptides, polypeptides, proteins, and peptidomimetics. Methods for preparing peptidomimetics are known in the art. In particular, a peptidomimetic can be derived as a retro-inverso analog of the peptide. Such retro-inverso analogs can be prepared according to methods known in the art (see, e.g., U.S. Pat. No. 4,522,752).

The term "polypeptide" as in "polypeptide operatively linked to a yeast protein" is also intended to encompass any amino acid sequence that, by virtue of its operative linkage to a cellular signal transduction-responsive protein generates a change in a detectable signal when the pathway is modulated. In certain embodiments, the polypeptide does so by conferring signal transduction responsiveness to cellular moieties that are capable of generating a detectable signal or are capable of causing a detectable signal to be generated downstream, and that are not otherwise responsive to the signal transduction pathway. For example, in certain embodiments of the invention, the term "polypeptide" as used in this context includes, but is not limited to, a transcription factor (e.g., an endogenous yeast transcription factor), a chimeric transcription factor, an enzyme (e.g., an endogenous yeast enzyme), a protein required for cell viability, or an indicator molecule (e.g., GFP).

The term "indicator molecule" as used herein refers to a polypeptide which provides a detectable signal, for example, green fluorescent protein (GFP).

The term "stimulation" (as in "stimulation of a pheromone response/signal transduction pathway of a yeast cell") is intended to refer to "switching on" the yeast signal transduction cascade. The signal transduction cascade can be switched on by external signals that interact with cell receptors, e.g., ligand binding to a G-protein coupled receptor. The term "stimulation" is also intended to encompass switching on the yeast signal transduction cascade by any other process including, for example, a process similar to the process by which phorbol esters activate the calcium dependent signal transduction pathway of T cell receptors.

The term "functionally integrated" (as in a receptor that is "functionally integrated into a signal transduction pathway in a cell" or "functionally integrated into a yeast pheromone response pathway") is intended to refer to the ability of the receptor to be expressed at the surface of the cell and the ability of the expressed receptor to bind to modulators (e.g., a ligand of the receptor) and transduce signals into the cell via components of a signal transduction pathway of the cell. For example, a G protein-coupled receptor (GPCR) which is functionally integrated into an endogenous pheromone response pathway of a yeast cell is expressed on the surface of the yeast cell, couples to a G protein of the pheromone response pathway within the yeast cell, and transduces a signal in that yeast cell upon binding of a modulator to the receptor.

The term "modulation" is intended to encompass, in its various grammatical forms (e.g., "modulated", "modulation", "modulating", etc.), up-regulation, induction, stimulation, potentiation, localization changes (e.g., movement of a protein from one cellular compartment to another) and/or relief of inhibition, as well as inhibition and/or down-regulation.

The term "activity" as in "the activity of the yeast protein is modulated" refers to the responsiveness or sensitivity of the yeast protein resulting from stimulation of a yeast signal transduction pathway (e.g., the pheromone response pathway). Modulation of the yeast protein activity may occur by any biochemical mechanism. For example, and without being bound by theory, the activity of the yeast protein may be modulated by changing the protein from an inactive or "dormant" state to an active or "sensitized" state. A protein may be changed from an inactive state to an active state, for example, by a conformational change in the protein structure. In an inactive state, the protein may have conformation X, but in an activated state, the protein assumes conformation Y, which enables the protein to become active/functional. Other mechanisms that involve modulating protein activity include those in which the protein is associated with a second agent that sequesters or inhibits the protein activity. The term "agent" as used herein refers to a protein, peptide, or a factor that associates with the protein and inhibits the functional activity of the protein. Release of the associated agent from the protein allows the protein to become active/functional. Accordingly, the phrase "activity of the yeast cell is modulated" also refers to activation by release, relief, or removal of an inhibitory agent associated with the protein.

The term "directly" as in "the activity of the yeast protein is modulated directly" refers to a process of one or more steps whereby the yeast protein is activated by stimulation of the signal transduction pathway (e.g., pheromone response pathway). For example, in one embodiment of the invention, upon stimulation of the signal transduction pathway, the yeast protein undergoes a change in activity/state ultimately causing, for example, transcription of a gene.

The term "indirectly" as in "the activity of the yeast protein is modulated indirectly" refers to a mechanism whereby stimulation of the signal transduction pathway modulates the endogenous wild type yeast protein, which in turn acts upon and modulates the activity of its corresponding mutant yeast protein component of the fusion protein. Because the wild type yeast protein is sensitive to stimulation of the signal transduction pathway, and the corresponding mutant yeast protein is not sensitive, the activity of the mutant yeast protein is said to be "indirectly modulated" upon stimulation of the signal transduction pathway. The endogenous wild type yeast protein may modulate the activity of the mutant yeast protein by any of the mechanisms described above with regard to direct modulation.

To summarize, the signal transduction responsive activity of the fusion protein can be supplied in cis (from the wild type yeast protein component of the chimeric fusion protein) or in trans (from the endogenous wild type yeast protein).

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signal transduction pathway" refers to the components involved in "signal transduction" of a particular signal into a cell. The term "endogenous signal transduction pathway" indicates that some or all of the components of the signal transduction pathway are naturally-occurring components of the cell. An example of such a pathway is the endogenous pheromone response pathway of yeast.

The term "detecting an alteration in a signal produced by a signal transduction pathway" (e.g., a yeast pheromone response pathway) is intended to encompass the detection of alterations in second messengers produced upon activation of components of the signal transduction pathway, alterations in gene transcription induced upon activation of components of the signal transduction pathway, and/or alterations in the activity of a protein(s) upon activation of components of the signal transduction pathway. In some embodiments, the term "detecting an alteration in a signal produced by an endogenous signal pathway" is not, however, intended to encompass detecting alterations in the level of expression of an exogenous reporter gene that has been introduced into the cell or the activity of the reporter gene product. Moreover, the term "detecting an alteration in a signal produced by a signal transduction pathway" is not intended to encompass assaying general, global changes to the cell. Rather, this term indicates that a specific signal associated with the signal transduction pathway is assayed.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

The term "wild type protein" as used herein refers to unmodified, naturally occurring cellular proteins (e.g., a yeast protein) or fragments thereof.

The term "mutated protein" or "mutant protein" as used herein refers to a cellular proteins (e.g., a yeast protein), or fragment thereof, that has been modified by addition, deletion or substitution of amino acid residues in the protein. Preferably, the mutated protein is derived from the wild type protein. For example, in the case of the pheromone responsive wild type Fus3 yeast protein, the mutant thereof may comprise an amino acid substitution at positions 42, 180 or 182, or at positions 180 and 182 in the wild type amino acid sequence.

The term "compound" as used herein (e.g., as in "test compound") is meant to include both exogenously added test compounds and peptides endogenously expressed from a peptide library. For example, in certain embodiments, the reagent cell also produces the test compound which is being screened. The reagent cell can produce, e.g., a test polypeptide, a test nucleic acid and/or a test carbohydrate which is screened for its ability to modulate the receptor/channel activity. In such embodiments, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds, for example small organic molecules. "Non-peptidic compounds" also are intended to include natural products.

The term "receptor effector" is intended to include agonists and antagonists that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence of the natural ligand, either to enhance or inhibit signaling by the natural ligand. The term "antagonists" as used herein refers to molecules that block or decrease the signal transduction activity of a receptor; e.g., they can competitively, non competitively, and/or allosterically inhibit signal transduction from the receptor.

The term "agonist" as used herein refers to agents which: induce activation of receptor signaling pathways, e.g., such as by mimicking a ligand for the receptor; potentiate the sensitivity of the receptor to a ligand, e.g., lower the concentrations of ligand required to induce a particular level of receptor-dependent signaling; or otherwise enhance the signal transduction activity of a receptor.

The terms "receptor activator" and "surrogate ligand" as used herein refer to an agonist which induces signal transduction from a receptor.

"Orphan receptor" is a designation given to a receptor for which no specific natural ligand has been described and/or for which no function has been determined.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

The term "heterologous promoter" as used herein, refers to a promoter that does not naturally regulate the gene to which the heterologous promoter is operatively linked. For example, an endogenous yeast gene that is not normally responsive to a signal transduction pathway of the yeast cell (e.g., a yeast pheromone response pathway) can be operatively linked to a heterologous promoter, also not normally responsive to signals produced by the transduction pathway. A fusion protein of the invention, which is engineered to be responsive to the signal transduction pathway, is used to confer signal transduction responsiveness to the endogenous yeast gene through association of the binding site of the heterologous promoter with a region of the fusion protein.

The term "indicator gene" as used herein refers to an expressible (e.g., able to be transcribed and (optionally) translated) DNA sequence which is expressed in response to activation of the fusion protein of the invention. Exemplary indicator genes include unmodified endogenous genes operatively linked to heterologous promoters.

The terms "reporter gene" and "reporter gene construct" are used interchangeably herein to refer to an indicator gene operatively linked to at least one transcriptional regulatory sequence. Transcription of the reporter gene is controlled by the transcriptional regulatory sequence to which it is operatively linked. Exemplary transcriptional control sequences are promoter sequences. Examples of promoters include, but are not limited to, Gal1, Gal10, Mel and LexA operator. The activity of at least one or more of these control sequences is dependent on the activity of a fusion protein of the current invention, in contrast to the natural pheromone regulation of the reporter genes known in the art, (e.g., Fus1-lacZ, Fus1-HIS3, etc. see, e.g., U.S. Pat. Nos. 5,401,629 and 5,691,188). A reporter gene is also meant to include a promoter-reporter gene construct which is heterologously expressed in a cell.

The terms "transcriptional control element" and "transcriptional regulatory element" are used interchangeably herein, and are intended to encompass any moiety which controls/regulates transcription of a gene to which it is operatively linked, including, but not limited to, promoters, operators and enhancers which are responsive to the fusion proteins of the invention.

The term "chimeric nucleic acid construct" is intended to refer to a nucleic acid molecule, preferably DNA, composed of at least two discrete segments. These segments are operatively linked such that upon expression of the construct, a fusion protein is produced. The fusion protein comprises a first polypeptide encoded by the first segment and a second polypeptide encoded by the second segment. The first segment of the chimeric construct encodes a yeast protein responsive to a yeast signal transduction pathway, for example, Fus3, or a mutation thereof, in the case of a pheromone response pathway. The second segment encodes a polypeptide that causes a detectable signal to be generated upon stimulation of the signal transduction pathway. Examples of the polypeptides include, but are not limited to, an endogenous yeast transcription factor, a chimeric transcription factor, an enzyme, a protein required for yeast cell viability, or an indicator molecule.

The term "derived from" as used in the context of chimeric nucleic acid constructs is intended to indicate that, for example, the first and second segments have the same or a substantially homologous nucleotide sequence as all or a part of first and second genes, respectively. Similarly, the term "derived from" as used in the context of a polypeptide sequence derived from another polypeptide is intended to indicate that the first polypeptide has the same or a substantially homologous amino acid sequence as all or a part of the second polypeptide.

As used herein, "heterologous DNA" or "heterologous nucleic acid" includes DNA that does not occur naturally as part of the genome in which it is present, or which is found in a location or locations in the genome that differs from that in which it occurs in nature. Heterologous DNA is DNA that is not naturally occurring in that position or is not endogenous to the cell into which it is introduced, but has been obtained from another cell. Generally, although not necessarily, such DNA encodes proteins that are not normally produced by the cell in which it is expressed. Heterologous DNA can be from the same species, although in preferred embodiments, it is from a different species. In particularly preferred embodiments, it is mammalian, e.g., human. Heterologous DNA may also be referred to as foreign DNA. Any DNA that one of skill in the art would recognize or consider as heterologous or foreign to the cell in which it is expressed is herein encompassed by the term heterologous DNA. Examples of heterologous DNA include, but are not limited to, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

To determine the percent homology of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4, and a length weight of 1, 2, 3, 4, 5, or 6. In another embodiment, the percent identity between two nucleotide sequences is determined using the GAP program in the GCG software package, using a NWSgapdna.CMP matrix and a gap weight of 40, 50, 60, 70, or 80, and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12, and a gap penalty of 4.

The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to NIP2b, NIP2cL, and NIP2cS nucleic acid molecules of the invention: BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes. A "heterologous receptor" is a specific embodiment of a "heterologous protein", wherein the heterologous receptor is encoded by heterologous DNA and, upon expression of this heterologous DNA in a recombinant cell, the heterologous receptor is expressed in the recombinant cell.

The term "pheromone system protein surrogate" (abbreviated as "PSP surrogate") is intended to refer to a heterologous protein in a yeast cell which is functionally homologous to a yeast protein of the pheromone response pathway (i e., the PSP surrogate is functionally integrated into the yeast pheromone system pathway). Examples of PSP surrogates, and methods of preparing yeast cells comprising such PSP surrogates, are described in detail in PCT Publication WO 94/23025. Preferred PSP surrogates include G protein-coupled receptors, G proteins, proteases, kinases, farnesyltransferases, carboxymethyltransferases, ABC transporters and cyclins.

The term "autocrine cell", as used herein, refers to a cell which produces a substance which can stimulate a receptor located on or within the same cell as that which produces the substance. For example, wild-type yeast MATα and MATa cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

II. General Overview of Assay

As set out above, the invention relates to methods for identifying compounds from among a set or collection or library of one or more compounds that modulate the activity of a signal transduction pathway in a cell. The pathway may be an endogenous signal transduction pathway within the cell (for example, the pheromone response pathway in a yeast cell), or may comprise one or more surrogate components which function in place of a natural component of the pathway.

The method of the present invention makes use of a cell that comprises a polypeptide made responsive to the signal transduction pathway through operative linkage to a component of the pathway, such that the polypeptide is capable of causing a detectable signal to be generated upon activation of the signal transduction pathway. In accordance with the method, the cell is contacted with a test compound, and the modulatory effect of the compound on the activity of the signal transduction pathway is assessed.

Test compounds which act as agonists are detected as compounds which cause an increase in detectable signal as compared with the signal in the absence of the test compound. In another aspect, the effect of the test compounds on cells that are essentially identical except for the presence or absence of a target protein (e.g., a receptor, an ion channel, or a signal transduction pathway component surrogate) can be detected. Compounds which act as antagonists are detected as those which cause a decrease in the detectable signal generated by an agonist or a natural stimulator of signal transduction pathway when compared with the same cell in the absence of the test compound.

Alternatively, the target specificity of the test compound may be assessed by comparing the detectable signals generated in cells which differ only in the surrogate component of the signal transduction pathway. For example, cells which comprise different functionally coupled G protein-coupled receptors (GPCRs) may be compared in this way. Differences in detectable signal may then be ascribed to the GPCRs and may be distinguished from effects due to components present in each cell. In another embodiment, the cells may differ in that one cell comprises a functional surrogate signal transduction component (e.g., mammalian GPCR) whereas the other is identical except that the natural component is substituted for the functional surrogate.

In certain embodiments, a test compound is exogenously added, and its ability to modulate the activity of the target receptor or ion channel is scored in the assay. In other embodiments, the cells are engineered to express additionally a test polypeptide which can be assayed for its ability to interact with the receptor or ion channel. In those embodiments, the assay provides a population of cells which express a library of peptides which include potential receptor/channel effectors, and those peptides of the library which either agonize or antagonize the receptor or channel function can be selected and identified by sequence.

The ability of particular compounds to modulate the signal transduction activity of target receptor or channel can be scored for by detecting up or down-regulation of a detection signal. For example, second messenger generation (e.g. GTPase activity, phospholipid hydrolysis, or protein phosphorylation patterns) can be measured directly. In other embodiments, transcription of an endogenous gene or activity of an endogenous protein is used as a detectable readout. Alternatively, the use of an indicator gene can provide a convenient readout. In other embodiments, a detection means consists of a reporter gene. In any event, a statistically significant change in the detection signal can be used to facilitate identification of compounds which modulate receptor or ion channel activities.

By this method, compounds which induce a signal pathway from a particular receptor or channel can be identified. If a test compound does not appear to induce the activity of the receptor/channel protein, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

The method of the present invention is useful for identifying compounds that interact with any receptor protein whose activity ultimately induces a signal transduction cascade in the host cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone, or other nuclear receptors. In certain embodiments the method described herein is used for identifying ligands for "orphan receptors" for which no ligand is known.

In embodiments utilizing an "autocrine cell" of the present invention, and in which cell surface receptors are the assay targets, it will be desirable for each of the peptides of the peptide library to include a signal sequence for secretion. In certain embodiments the expression of such a signal sequence may ensure appropriate transport of the peptide to the endoplasmic reticulum, the golgi, and ultimately to the cell surface. When a yeast cell is the host cell, in certain embodiments, the signal sequence will transport peptides to the periplasmic space, however, such transport may not be necessary to achieve autocrine stimulation.

Any transfectable cell that can express the desired cell surface protein in a manner such the protein functions to transduce intracellularly an extracellular signal may be used. Similarly, any cell surface protein that is known to those of skill in the art or that may be identified by those of skill in the art may used in the assay. The cell surface protein may be endogenously expressed on the selected cell or it may be expressed from cloned DNA.

III. Chimeric Nucleic Acid Constructs Expressing Fusion Proteins that Confer Signal Transduction Responsiveness In one aspect, the invention provides chimeric nucleic acid constructs that express fusion proteins that are responsive to cellular signal transduction pathways. Expression of the fusion protein need not be constitutive, although it is important to note that the activity of the fusion protein, and not its expression, is responsive to the signal transduction pathway. The constructs comprise a first segment comprising a nucleotide sequence encoding a cellular protein that is responsive to a cellular signal transduction pathway, wherein the activity of the protein is modulated directly or indirectly upon stimulation of a cellular signal transduction pathway, and a second segment comprising a nucleotide sequence encoding a polypeptide that causes a detectable signal to be generated upon modulation of the transduction pathway responsive protein. The fusion protein expressed by the chimeric construct comprises the signal transduction-responsive protein operatively linked to the polypeptide. Thus, the fusion protein is responsive to activation/stimulation of the signal transduction pathway by virtue of the component comprising the cellular protein that is responsive to the cellular signal transduction pathway. The polypeptide can be a cellular transcription factor, a chimeric transcription factor, an enzyme, a protein required for cell viability, or an indicator molecule.

In a preferred embodiment, the cell is a yeast cell. Yeast proteins that are responsive to yeast signal transduction pathways include, but are not limited to, Fus3, Hog1, Kss1, Mpk1, Smk1, Bem1, Cdc24, Cdc42, Dig1, Dig2, Far1, Gpa1, Msg5, Ste4, Ste5, Ste7, Ste11, Ste12, Ste18, Ste20 and Sst2. In another preferred embodiment, the yeast signal transduction pathway is the yeast pheromone response pathway.

Yeast proteins that are sensitive/responsive to the pheromone response pathway include kinases that are homologous to the highly conserved family of kinases called mitogen activated protein (MAP) kinases. Members of the MAP kinase family are activated by a variety of extracellular agents and influence cellular proliferation and differentiation. In *Saccharomyces cerevisiae* five MAP kinase gene homologs have been identified, (Davis et. al., (1995) *Mol. Reprod. Dev.* 42, 459–467).

Preferred pheromone sensitive/responsive yeast proteins include Fus3, Kss1, Bem1, Cdc24, Cdc42, Dig1, Dig2, Far1, Gpa1, Msg5, Ste4, Ste5, Ste7, Ste11, Ste12, Ste18, Ste20 and Sst2. Especially preferred for the practice of the invention is Fus3, which is activated during the pheromone response pathway and, based on the high degree of homology with MAP kinase, may function in a similar kinase cascade (see, e.g., Errede et. al., (1995) *Mol. Reprod. and Dev.* 42, 477–45 and Gartner et. al., (1992) *Genes and Dev.* 6, 1280–1292). The gene encoding Fus3 was cloned by Fujimura (who referred to the gene as Dac2) (see Fujimura (1990) *Curr. Genet.* 18, 395–400). Standard molecular biology procedures are used for making fusion proteins comprising Fus3 operatively linked to a polypeptide, as described in Example 1. Far1, Ste5, Ste11 and Ste12, other pheromone-responsive yeast proteins, are also particularly preferred.

In one embodiment, the fusion protein comprises a wild type yeast protein that is responsive to a yeast signal transduction pathway. In another embodiment, the fusion protein comprises a mutant yeast protein derived from the wild type protein. For example, in the case of Fus3, a pheromone responsive yeast protein, the fusion protein can comprise a mutant Fus3 protein comprising amino acid substitutions at positions 42, 180, 182, or at positions 180 and 182 as compared to the wild type Fus3 amino acid sequence. Exemplary amino acid substitutions in the Fus3 wild type amino acid sequence, include, but are not limited to, Lys42Arg, Thr180Val, Thr180Glu, Tyr182Val, and Tyr182Asp. The production of mutant pheromone responsive Fus3 yeast proteins is described in Example 2.

In one embodiment, the second segment of the chimeric nucleic acid construct comprises a nucleotide sequence that encodes a cellular transcription factor. The fusion protein expressed by the chimeric nucleic acid construct comprises the signal transduction responsive protein operatively linked to the transcription factor. Polypeptides which can function as transcription factors to activate transcription in prokaryotic cells are well known in the art. Any wild type transcription factor of interest may be operatively linked to the signal transduction responsive protein for use in the method of the invention. In the case of a yeast signal transduction pathway, transcription factors suitable for use in the present invention include, but are not limited to, the endogenous yeast transcription factors Ste12, Gal4, Pho4, Gcn4, Hap1, Adr1, Ace2, Cup2, Swi5 and Bas1.

In another embodiment, the second segment of the chimeric nucleic acid construct comprises a nucleotide sequence that encodes a chimeric transcription factor. The second segment comprises a third segment comprising a nucleotide sequence encoding a DNA binding domain, and a fourth segment comprising a nucleotide sequence encoding a transcriptional activation domain. Thus, the fusion protein expressed by the chimeric nucleic acid construct comprises a signal transduction-responsive protein operatively linked to a chimeric transcription factor comprising a DNA binding domain operatively linked to a transcriptional activation domain.

Chimeric transcription factors can be constructed using standard molecular biology techniques as described in Example 1. The DNA binding domain and the transcriptional activation domain of the chimeric transcription factor can be derived either from the same protein, e.g., a prokaryotic protein, or from different proteins, e.g., a prokaryotic protein and a eukaryotic protein, or two different proteins from the same organism.

DNA binding domains that bind to specific regulatory sequences are also well known in the art (see, e.g., Keegan et al., (1988), *Science*, 231, 699–704; Hope et al., (1986) *Cell*, 46, 885–894 and Ma et al., (1987) *Cell* 51, 113–119). A selected transcriptional activation domain can be paired with a DNA binding domain to activate transcription (Brent et al., (1985) *Cell* 43, 729–736; see also U.S. Pat. No. 4,833,080 to Brent et al. which discloses regulation of eukaryotic gene expression using a two component chimeric fusion protein consisting of a DNA binding domain and a transcriptional activation domain) providing the nucleotide sequence to be transcribed is operatively linked to a promoter sequence recognized by the selected DNA binding domain. Residues 1–147 of Gal4 confer sequence specific DNA binding (See Carey et al., (1989) *J. Mol. Biol.* 209, 423–432). Residues 1–87 of the bacteria repressor LexA also confer sequence specific DNA binding activity (See Olesen et al., (1990) *Genes Dev.* 4, 1714–1729 and Brent et al., (1985) *Cell* 43, 729–236). DNA binding domains that can be used in the invention include, but are not limited to, LexA, Gal4, Adr1, Ace2, Cup2, Bas1, Gcn4, Swi5, Pho4, Hap1, and LacI.

Transcriptional activation domains of many DNA binding proteins have been described and have been shown to retain their activation function when the domain is transferred to a heterologous polypeptide. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include VP16 and amino acid residues 753–881 of GAL4. Examples of proline-rich activation domains include amino acid residues 399–499 of CTF/NF1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Sp1. The amino acid sequences of each of the above described regions, and of other useful transcriptional activation domains, are disclosed in Seipel, K. et al. (*EMBO J.* (1992) 13:4961–4968).

In addition to previously described transcriptional activation domains, novel transcriptional activation domains, which can be identified by standard techniques, are within the scope of the invention. The transcriptional activation ability of a polypeptide can be assayed by operatively linking a transcriptional activation domain to a DNA binding domain to form a chimeric transcription factor. The activity of the transcription factor can be determined using the assays described in Example 1, and the amount of transcription of a target sequence can be determined. Preferred transcriptional activation domains include but are not limited to the B42, Gal4, Adr1 Ace2, Cup2, Bas1, Gcn4, Swi5, Pho4, Hap1, VP16, and Ste 12. The B42, VP16, Gal4, and Ste12 transcriptional activation domains are particularly preferred.

In the case of activation of a yeast pheromone response pathway in a yeast cell, the activity of the pheromone responsive yeast protein is modulated directly or indirectly, thereby causing the chimeric transcription factor to activate transcription of a gene that produces a detectable protein. For example, in a preferred embodiment, the first segment of the construct encodes wild type Fus3 and the second segment encodes a chimeric transcription factor; that is, the second segment comprises a third segment that encodes the entire prokaryotic protein LexA as the DNA binding domain, and a fourth segment that encodes an 88 amino acid segment of an acidic *E. coli* peptide (B42AD) as the transcriptional activation domain. Upon expression of the chimeric construct, signaling through the pheromone response pathway modulates Fus3 thereby activating the LexA-B42AD component (the "chimeric transcription factor") of the fusion protein, to which component Fus3 is operatively linked. The chimeric transcription factor activates transcription of the gene which is operatively linked to a promoter which contains the binding sites for LexA and LexA operators. Thus, in the case of the lacZ indicator gene under the control of the LexA operator (p8op-lacZ), the LexA-B42AD-Fus3 fusion protein binds to LexA binding site in the promoter and induces expression of the lacZ gene. β-Galactosidase is the detectable signal resulting from expression of the lacZ gene. Exemplary chimeric transcription factors include, but are not limited to, LexA-B42AD, Gal4DBD-B42AD, Gal4DBD-VP16AD and Gal4DBD-Gal4ADII.

In certain embodiments of the invention wherein the second segment of the chimeric nucleic acid construct encodes a cellular transcription factor, or a chimeric transcription factor, the fusion protein resulting from expression of the construct can be used to confer signal transduction-responsiveness on indicator genes, including heterologous genes as well as endogenous yeast genes, that are not normally responsive to the signal transduction pathway, as described in Examples 1 and 2. Examples of indicator genes suitable for use in accordance with the invention include ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ, LEU1, LEU2, LEU4, luciferase, LYS2, MAL, MEL MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10. Preferred indicator genes include CAT, GAL1, GAL7, GAL10, GFP, HIS3, lacZ, luciferase, LEU2, MEL, PHO5, and URA3.

In practicing one embodiment of the invention, a reporter gene construct is inserted into the reagent cell that will produce a detection signal upon activation of the chimeric fusion protein. Typically, the reporter gene construct will include an indicator gene in operative linkage with one or more transcriptional control elements, the activity of which is indirectly regulated by the signal transduction activity of the target receptor, with the level of expression of the reporter gene providing the receptor-dependent detection signal. The amount of transcription from the indicator gene may be measured using any method known to those of skill in the art to be suitable.

Transcriptional control elements for use in the reporter gene constructs, or for modifying the genomic locus of an indicator gene include, but are not limited to, promoters, enhancers, and operators, the activities of which are responsive to the polypeptide comprising the transcription factor/chimeric transcription factor component of the chimeric fusion protein of the invention. That is, the transcriptional control elements are not normally responsive to the signal transduction pathway of the cell, but are made responsive by interaction with the fusion protein.

In another embodiment, the second segment of the nucleic acid construct of the invention encodes a polypeptide that comprises an enzyme. The fusion protein expressed by the chimeric construct comprises the yeast protein operatively linked to the enzyme. Upon stimulation of the signal transduction pathway, the yeast protein is modulated and confers an ability to the enzyme to directly produce a detectable signal. By operatively linking the yeast cell protein to the enzyme, the method of the invention eliminates the requirement for a reporter gene construct. Instead, stimulation of the signal transduction pathway is monitored directly as a result of the enzyme producing an end product which provides the detectable signal. For example, the enzyme can be a conventional enzyme that catalyzes the conversion of a substrate to a product and thereby generate a detectable signal, such as, e.g., a change in color, fluorescence, or luminescence. Examples of such enzymes include CAT (chloramphenicol acetyl transferase) (Alton and Vapnek (1979), *Nature* 282: 864–869); luciferase, β-galactosidase; firefly luciferase (deWet et al. (1987), *Mol. Cell. Biol.* 7:725–737); bacterial luciferase (Engebrecht and Silverman (1984), *P.N.A.S.* 1: 4154–4158; Baldwin et al. (1984), *Biochemistry* 23: 3663–3667); alkaline phosphatase (Toh et al. (1989) *Eur. J. Biochem.* 182: 231–238, Hall et al. (1983) *J. Mol. Appl. Gen.* 2: 101), human placental secreted alkaline phosphatase (Cullen and Malim (1992) *Methods in Enzymol.* 216:362–368); β-lactamase, etc.

Alternatively, the enzyme can be a metabolic enzyme that relieves a cell's nutritional requirement and/or provides resistance to a drug. For example, in one embodiment, the imidazoleglycerol phosphate dehydratase (IGP dehydratase) (ie., the His3 enzyme) can be used in the chimeric fusion protein of the invention. In the simplest case, the cell is auxotrophic for histidine (requires histidine for growth) in the absence of activation. Activation of the His3 enzyme, through association with the signal transduction responsive protein component of the fusion protein, causes the cell to become prototrophic for histidine (does not require histidine). Thus the selection is for growth in the absence of histidine. Since only a few molecules per cell of IGP dehydratase are required for histidine prototrophy, the assay is very sensitive.

In yet another embodiment, the second segment of the nucleic acid construct of the invention encodes a polypeptide that comprises a protein required for cell viability. The fusion protein expressed by the chimeric construct comprises the signal transduction responsive protein operatively linked to the protein required for cell viability. Detection of cell growth and viability can be used as an effective screening procedure. In a yeast embodiment, to determine cell viability, a pheromone responsive yeast protein is operatively linked to a polypeptide that confers cell growth or viability to the yeast cell (See Example 3). When the pheromone response pathway is stimulated, the yeast protein confers a signal pathway dependent prototrophy on the yeast cell to enable the yeast cell to grow on media plates on which it would not typically be able to grow. As exemplified in Example 3, a yeast protein (e.g., Ste11) that is operatively linked to His3. This chimeric construct can be transformed into a suitable yeast strain, e.g., a strain auxotrophic for histidine. Upon stimulation of the pheromone response pathway, the chimeric construct confers pheromone pathway dependent histidine prototrophy on the yeast cell which allows the strain to grow on histidine minus media plates.

Examples of polypeptides required for cell growth include, but are not limited to, Ade1, Ade2, Ade3, Ade4, Ade5, Ade7, Ade8, Asp3, Arg1, Arg3, Arg4, Arg5, Arg6, Arg8, Aro2, Aro7, Bar1, Cho1, Cys3, Gal1, Gal7, Gal10, His1, His3, His4, His5, Hom3, Hom6, Ilv1, Ilv2, Ilv5, Ino1, Ino2, Ino4, Leu1, Leu2, Leu4, Lys2, Mal, Mel, Met2, Met3, Met4, Met8, Met9, Met14, Met16, Met19, Ole1, Pho5, Pro1, Pro3, Thr1, Thr4, Trp1, Trp2, Trp3, Trp4, Trp5, Ura1, Ura2, Ura3, Ura4, Ura5, Ura10, Cdc25, Cyr1 and Ras. Particularly preferred polypeptides that confer growth and cell viability include Gal1, His3, Leu2, Mel, Ura3, Cdc25, Cyr1 and Ras.

Another example of a protein that is required for cell viability is Ras. In mammalian cells, Ras is a membrane associated GTPase that functions as a molecular switch to activate intracellular mitogen-activated protein kinase (MAPK) cascades and other effector pathways in response to a cellular signal. Activation of Ras into its GTP-bound conformation is directly controlled by specific guanine-nucleotide exchange factors (GEF's), which catalyze GDP release (See e.g., Fan et al. (1988) *Curr. Biol.* 13: 935–938). Several Ras-specific GEFs that relate to the yeast protein Cdc25, have been described. Proteins involved in the Ras cell signaling pathway or cascade are art recognized. See, e.g., Murray, A. and Hunt, T. eds. The Cell Cycle: An Introduction (W.H. Freeman and Company, New York) pp. 109–110. Briefly, the Ras cell signaling cascade begins with cell activation, e.g., cell activation by a growth factor, and activation of the growth factor receptor. Receptor binding leads to the binding of adaptor proteins, for example, GRB2. The adaptor proteins activate guanine nucleotide-exchange proteins and GTPase activating proteins, e.g., p120-GAP, which, in turn, activate small G proteins such as Ras. Ras, in turn, induces activation and phosphorylation of Raf, MEK, p44 and p42 MAP kinases (ERK1 and ERK2). Raf is the first member of the protein kinase cascade which ultimately leads to the phosphorylation and activation of MAP kinase. Activation of MAP kinase leads to its translocation into the nucleus where it induces transcription.

The activities of RAS genes are essential for viability of a yeast cell. Although a yeast cell is still viable upon deletion of either the RAS1 or RAS2 genes, deletion of both genes is lethal. Moreover, deletion of the RAS2 gene is lethal for a cell grown in media consisting of nonfermentable carbon sources, such as glycerol and ethanol. In addition, expression of the mammalian Ras protein is capable of rescuing the yeast cell from lethality. (T. Kataoka, et al., (1984) *Cell* 37:437; T. Kataoka, et al., (1985) *Cell* 40:19; D. DeFeo-Jones et al., (1985) *Science* 228:179; and K. Tatchell et al. (1985) *PNAS* 82:3785). Effective interaction between Ras and its downstream target, adenylyl cyclase, which is localized on the membrane, is essential. Thus, the membrane association of Ras proteins is crucial to cell viability (T. Toda et al. (1985) *Cell* 40:27; J E Buss et al. (1989) *Science*, 243:1600; and J F Hancock et al., (1989) *Cell*, 57:1167).

Operatively linking a yeast protein to a Ras protein whose localization to the membrane is dependent on the activation of a signal transduction pathway thus confers cell viability to a cell in which one or more RAS genes has been inactivated. Thus, in one embodiment, the yeast protein, e.g., a pheromone responsive yeast protein, is operatively linked to Ras. Upon stimulation of the pheromone response pathway, the activity of the yeast protein is modulated, which in turn modulates the activity of Ras. Ras subsequently activates other members of the cascade and ultimately confers cell growth. In a preferred embodiment, the pheromone responsive protein is Ste5.

The foregoing embodiments demonstrate that overall, the invention provides a rapid, reproducible, robust assay system that makes use of a fusion protein, the activity of which is responsive to a cellular signal transduction pathway (e.g., the pheromone response pathway in yeast cells), to confer signal transduction responsiveness on cellular moieities, including, but not limited to, indicator genes, transcription regulatory elements, enzymes, and proteins required for cell viability that are not otherwise responsive to the signal transduction pathway.

IV. Host Cells

Suitable host cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) *Cell* 23:175) CV-1 cells (ATCC CCL 70), L cells, C127, 3T3, Chinese hamster ovary (CHO), HeLa, HEK-293, SWISS 3T3, and BHK cell lines.

If yeast cells are used, the yeast may be of any species which are cultivable and in which an exogenous receptor can be made to engage the appropriate signal transduction machinery of the host cell. Suitable species include *Kluyveromyces lactis, Schizosaccharomyces pombe,* and *Ustilago maydis; Saccharomyces cerevisiae* is preferred. Other yeast which can be used in practicing the present invention are *Neurospora crassa, Aspergillus niger, Aspergillus nidulans, Pichia pastoris, Candida tropicalis,* and *Hansenula polymorpha.* The term "yeast", as used herein, includes not only yeast in a strictly taxonomic sense, i.e., unicellular organisms, but also yeast-like multicellular fungi or filamentous fungi.

It will be understood that to achieve selection or screening, the host cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is preferred.

A variety of complementations for use in the subject assay can be constructed. Indeed, many yeast genetic complementations with mammalian signal transduction proteins have been described in the art. For example, Mosteller et al. (1994) *Mol. Cell Biol.* 14:1104–12 demonstrates that human Ras proteins can complement loss of ras mutations in *S. cerevisiae.* Moreover, Toda et al. (1986) *Princess Takamatsu Symp* 17: 253–60 have shown that human Ras proteins can complement the loss of Ras1 and Ras2 proteins in yeast, and hence are functionally homologous. Both human and yeast Ras proteins can stimulate the magnesium and guanine nucleotide-dependent adenylate cyclase activity present in yeast membranes. Ballester et al. (1989) *Cell* 59: 681–6 describe a vector to express the mammalian GAP protein in the yeast *S. cerevisiae.* When expressed in yeast, GAP inhibits the function of the human Ras protein, and complements the loss of IRA1. IRA1 is a yeast gene that encodes a protein with homology to GAP and acts upstream of Ras. Mammalian GAP can therefore function in yeast and interact with Ras yeast. Wei et al. (1994) *Gene* 151: 279–84 describes that a human Ras-specific guanine nucleotide-exchange factor, Cdc25GEF, can complement the loss of Cdc25 function in *S. cerevisiae.* Martegani et al. (1992) *EMBO J* 11: 2151–7 describe the cloning by functional complementation of a mouse cDNA encoding a homolog of Cdc25, a *Saccharomyces cerevisiae* Ras activator. Vojtek et al. (1993) *J. Cell Sci.* 105: 777–85 and Matviw et al. (1992) *Mol. Cell Biol.* 12: 5033–40 describe how a mouse CAP protein, e.g., an adenylyl cyclase associated protein associated with Ras-mediated signal transduction, can complement defects in *S. cerevisiae.* Papasavvas et al. (1992) *Biochem. Biophys. Res. Commun.* 184:1378–85 also suggest that inactivated yeast adenyl cyclase can be complemented by a mammalian adenyl cyclase gene. Hughes et al. (1993) *Nature* 364: 349–52 describe the complementation of byr1 in fission yeast by mammalian MAP kinase (MEK). Parissenti et al. (1993) *Mol Cell Endocrinol* 98: 9–16 describe the reconstitution of bovine protein kinase C (PKC) in yeast. The $Ca^{2+}$ and phospholipid-dependent Ser/Thr kinase PKC plays important roles in the transduction of cellular signals in mammalian cells. Marcus et al. (1995) *P.N.A.S.* 92: 6180–4 suggest the complementation of shk1 null mutations in *S. pombe* by either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of an inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

In certain embodiments (particularly those in which an autocrine peptide library is employed), the growth arrest consequent to activation of the pheromone response pathway is an undesirable effect since cells that bind agonists stop growing while surrounding cells that fail to bind peptides will continue to grow. The cells of interest, then, will be overgrown or their detection obscured by the background cells, confounding identification of the compound of interest. To overcome this problem the present invention teaches engineering the cell such that: 1) growth arrest does not occur as a result of exogenous signal pathway activation (e.g., by inactivation of the FAR1 gene); and/or 2) a selective growth advantage is conferred by activating the pathway (See, e.g., Example 3).

It is desirable that the exogenous receptor be exposed on a continuing basis to the test compound. Unfortunately, this is likely to result in desensitization of the pheromone response pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations, e.g., STE50, SGV1, BAR1, STE2, STE3, PIK1, MSG5, SIG1 and AFT1, have the similar effect of increasing the sensitivity of the bioassay. Thus desensitization may be avoided by mutating (which may include deleting) the SST2 gene so that it no longer produces a functional protein, or by mutating one of the other genes listed above.

V. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (Cloning Vectors: A Laboratory Manual, Elsevier, New York, 1985). Mammalian expression vectors may comprise non-transcribed elements such as an origin of replication, a suitable promoter and enhancer linked to the gene to be expressed, other 5' or 3' flanking nontranscribed sequences, 5' or 3' nontranslated sequences, such as necessary ribosome binding sites, a poly-adenylation site, splice donor and acceptor sites, and transcriptional termination sequences.

Preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

Transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al. (1978) Nature 273:111). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (1983, Mol. Cell Biol. 3:280). A useful system for stable high level expression of mammalian receptor cDNAs in C127 murine mammary epithelial cells can be constructed substantially as described by Cosman et al. (1986, Mol. Immunol. 23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs in S. cerevisiae (see, for example, Broach et al. (1983) in Experimental Manipulation of Gene Expression, ed. M Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., J. Biol. Chem. 255, 2073 1980) or other glycolytic enzymes (Hess et al., J. Adv. Enzyme Req. 7, 149 (1968); and Holland et al. Biochemistry 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose, galactose and melibiose utilization. Finally, promoters that are active in only one of the two haploid mating types may be appropriate in certain circumstances. Among these haploid-specific promoters, the pheromone promoters MFa1 and MFα1 are of particular interest.

In some instances, it may be desirable to use insect cells as the host cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

In certain embodiments, the host cell harbors a reporter gene construct containing an indicator gene in operative linkage with one or more transcriptional regulatory elements that associate with the chimeric fusion protein of the invention. Exemplary indicator genes include enzymes, such as luciferase, phosphatase, or β-galactosidase which can produce a spectrometrically active label, e.g., changes in color, fluorescence or luminescence, or a gene product which alters a cellular phenotype, e.g., cell growth, drug resistance or auxotrophy. For example, in certain embodiments, the indicator gene encodes a gene product selected from the group consisting of chloramphenicol acetyl transferase, β-galactosidase and secreted alkaline phosphatase. In still other embodiments, the indicator gene encodes a gene product which confers a growth signal. In yet another embodiment, the indicator gene encodes a gene product that permits prototrophic growth, or that confers sensitivity to drugs for counterselection purposes, e.g., canavanine or cycloheximide.

VI. Receptors

Receptor proteins (e.g., pheromone system protein surrogates) for use in the present invention can be any receptor or ion channel which interacts with an extracellular molecule (i.e., hormone, growth factor, peptide, ion) to modulate a signal in the cell. To illustrate, the receptor can be a cell surface receptor or, in other embodiments, an intracellular receptor. In certain embodiments, the receptor is a cell surface receptor, such as: a receptor tyrosine kinase, e.g., an EPH receptor; an ion channel; a cytokine receptor; a chemokine receptor; a growth factor receptor; or a G-protein coupled receptor, such as a chemoattractant peptide receptor, a neuropeptide receptor, a light receptor, a neurotransmitter receptor, or a polypeptide hormone receptor. In a preferred embodiment, the pheromone system protein surrogate to be assayed is selected from the group consisting of G protein-coupled receptors, G proteins, proteases, kinases, farnesyltransferases, carboxymethyltransferases, ABC transporters and cyclins. The different groups of receptors are described in detail below.

In addition, the subject assay can be used to identify ligands for an orphan receptor, i.e., a receptor with no known ligand, regardless of the class of receptors to which it belongs.

In those embodiments wherein the target receptor is a cell surface receptor and the cell expresses a peptide library, it may be desirable, in certain embodiments, for the peptides in the library to express a signal sequence to ensure that they are processed in the appropriate secretory pathway and thus are available to interact with receptors on the cell surface.

A. Cytokine Receptors

In one embodiment, the target receptor is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the Jak protein tyrosine kinase family, with resultant phosphorylation of the STAT transcriptional activator factors. IL-2, IL-4, IL-7 and Interferon γ have all been shown to activate Jak kinases (Frank et al. (1995) *Proc. Natl. Acad. Sci. USA* 92:7779–7783); Scharfe et al. (1995) *Blood* 86:2077–2085); (Bacon et al. (1995) *Proc. Natl. Acad. Sci. USA* 92:7307–7311); and (Sakatsume et al. (1995) *J. Biol. Chem.* 270:17528–17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al. (1995) *Proc. Natl. Acad. Sci.* 92:5482–5486) and (Musso et al. (1995) *J. Exp. Med.* 181:1425–1431). The Jak kinases have also been shown to be activated by numerous ligands that signal via cytokine receptors such as, growth hormone and erythropoietin and IL-6 (Kishimoto (1994) *Stem cells Suppl.* 12:37–44).

B. Nuclear Receptors.

In another embodiment, the target receptor is a nuclear receptor. The nuclear receptors may be viewed as ligand-dependent transcription factors. These receptors provide a direct link between extracellular signals, mainly hormones, and transcriptional responses. Their transcriptional activation function is regulated by endogenous small molecules, such as steroid hormones, vitamin D, ecdysone, retinoic acids and thyroid hormones, which pass readily through the plasma membrane and bind their receptors inside the cell (Laudet and Adelmant (1995) *Current Biology* 5:124). The majority of these receptors appear to contain three domains: a variable amino terminal domain; a highly conserved, DNA-binding domain and a moderately conserved, carboxyl-terminal ligand-binding domain (Power et al. (1993) *Curr. Opin. Cell Biol.* 5:499–504). Examples include the estrogen, progesterone, androgen, thyroid hormone and mineralocorticoid receptors. In addition to the known steroid receptors, at least 40 orphan members of this superfamily have been identified. (Laudet et al., (1992) *E.M.B.O. J.* 11:1003–1013). There are at least four groups of orphan nuclear receptors represented by NGF1, FTZ-F1, Rev-erbs, and RARs, which are by evolutionary standards, only distantly related to each other (Laudet et al. supra). While the steroid hormone receptors bind exclusively as homodimers to a palindrome of their hormone responsive element other nuclear receptors bind as heterodimers. Interestingly, some orphan receptors bind as monomers to similar response elements and require for their function a specific motif that is rich in basic amino-acid residues and is located corboxy-terminal to the DNA-binding domain (Laudet and Adelmant supra.)

C. Receptor Tyrosine Kinases.

In another embodiment, the target receptor is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., (1987) *Science* 238:1717–1720 and Lindberg and Hunter, (1990) *Mol. Cell. Biol.* 10:6316–6324). The functional domains of the kinase region of these three classes of receptor tyrosine kinases are encoded as a contiguous sequence (Hanks et al. (1988) *Science* 241:42–52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) *Science* 238:1717–1720), sequences have been reported for at least ten members of this family, not counting apparently orthologous receptors found in more than one species. Additional partial sequences, and the rate at which new members are still being reported, suggest the family is even larger (Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech. Dev.* 46:87–100; Xu et al. (1994) *Development* 120:287–299; Zhou et al. (1994) *J. Neurosci. Res.* 37:129–143; and references in Tuzi and Gullick (1994) *Br. J. Cancer* 69:417–421). Remarkably, despite the large number of members in the EPH family, all of these molecules were identified as orphan receptors without known ligands.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily recognizable, e.g., they are typically characterized by an extracellular domain containing a characteristic spacing of cysteine residues near the N-terminus and two fibronectin type III repeats (Hirai et al. (1987) *Science* 238:1717–1720; Lindberg et al. (1990) *Mol. Cell Biol.* 10:6316–6324; Chan et al. (1991) *Oncogene* 6:1057–1061; Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech. Dev.* 46:87–100; Xu et al. (1994) *Development* 120:287–299; Zhou et al. (1994) *J. Neurosci. Res.* 37:129–143; and references in Tuzi and Gullick (1994) *Br. J. Cancer* 69:417–421). Exemplary EPH receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention.

In exemplary embodiments, the detection signal is provided by detecting phosphorylation of intracellular proteins, e.g., MEKKs, MEKs, or Map kinases, or by the use of reporter constructs or indicator genes which include transcriptional regulatory elements responsive to c-fos and/or c-jun.

D. G Protein-Coupled Receptors.

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha ($\alpha$), beta ($\beta$) and gamma ($\gamma$) subunits, are complexed with the nucleotide guanosine diphosphate (GDP) and are in contact with receptors. When a hormone or other first messenger binds to a receptor, the receptor changes conformation and this alters its interaction with the G protein. This spurs the $\alpha$ subunit to release GDP, and the more abundant nucleotide guanosine triphosphate (GTP), replaces it, activating the G protein. The G protein then dissociates to separate the a subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct forms have been isolated. Although the greatest variability has been seen in the $\alpha$ subunit, several different $\beta$ and $\gamma$ structures have been reported. There are, additionally, many different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) *Cell* 72, 415; Kouba et al. *FEBS Lett.* (1993) 321, 173; and Birkenbach et al. (993) *J. Virol.* 67, 2209.

The "exogenous receptors" of the present invention may be any G protein-coupled receptor, preferably exogenous to the cell, which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (1h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include, but are not limited to: α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1 (IL-8 receptor A), CXCR2 (IL-8 receptor B), Delta Opioid receptor, Kappa Opioid receptor, mip-1alpha/RANTES receptor (CRR1), Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF1 receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein coupled receptors (GPCRs) are known in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include STE2, STE3, Gal1, and Gal10. Suitable signal sequences include those of STE2, STE3 and of other genes which encode proteins secreted by yeast cells. Preferably, when a yeast cell is used, the codons of the gene would be optimized for expression in yeast. See Hoekema et al., (1987) *Mol. Cell. Biol.*, 7:2914–24; Sharp, et al., (1986) 14:5125–43.

The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

In certain embodiments, if the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible. For example, the V–VI loop of a heterologous G protein coupled receptor could be replaced with that of the yeast STE2 or STE3 receptor).

In yet another embodiment, a compatible G protein can be provided. A compatible G protein for use in the instant assays can include a heterologous or chimeric G protein subunit (or subunits) such as those described in the art (see e.g., PCT PCT/US94/03143). Preferably, the yeast genome is modified so that it is unable to produce the yeast receptors which are homologous to the exogenous receptors in functional form.

F. Chemoattractant Receptors

An exemplary GPCR is the N-formyl peptide receptor (FPR), a classic example of a calcium mobilizing GPCR expressed by neutrophils and other phagocytic cells of the mammalian immune system (Snyderman et al. (1988) *In Inflammation*: Basic Principles and Clinical Correlates, pp. 309–323). N-formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyogenic infections. Similar signal transduction occurs in response to the inflammatory peptides C5a and Interleukin 8.

Two other formyl peptide receptor like (FPRL) genes have been cloned based on their ability to hybridize to a fragment of the FPR cDNA coding sequence. These have been named FPRL1 (Murphy et al. (1992) *J. Biol Chem.* 267:7637–7643) and FPRL2 (Ye et al. (1992) *Biochem Biophys Res. Comm.* 184:582–589). FPRL2 was found to mediate calcium mobilization in mouse fibroblasts transfected with the gene and exposed to formyl peptide. In contrast, although FPRL1 was found to be 69% identical in amino acid sequence to FPR, it did not bind prototype N-formyl peptides ligands when expressed in heterologous cell types. This lead to the hypothesis of the existence of an as yet unidentified ligand for the FPRL1 orphan receptor (Murphy et al. supra).

VII. Test Compounds

A. Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. *J. Am. Chem. Soc.* 114:10987; DeWitt et al. 1993. *Proc. Natl. Acad. Sci. USA:* 6909), peptoids (Zuckermann. 1994. *J. Med. Chem.* 37:2678) oligocarbamates (Cho et al. 1993. *Science* 261: 1303), and hydantoins (DeWitt et al. supra). Rebek et al. have described an approach for the synthesis of molecular libraries of small organic molecules with a diversity of 104–105 (Carell et al. 1994. *Angew. Chem. Int. Ed. Engl.* 33:2059; Carell et al. *Angew. Chem. Int. Ed. Engl.* 1994. 33:2061).

The compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. *Anticancer Drug Des.* 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. *Proc. Natl. Acad. Sci.* USA 91:11422; Horwell et al. 1996 *Immunopharmacology* 33:68; and in Gallop et al. 1994. *J. Med. Chem.* 37:1233. In addition, libraries such as those described in the commonly owned applications U.S. Ser. No. 08/864,241 now abandonded, U.S. Ser. No. 08/864,240 now U.S. Pat. No. 6,037,340 and U.S. Ser. No. 08/835,623 now abandonded can be used to provide compounds for testing in the present invention.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat No. '409), plasmids (Cull et al. (1992) *Proc. Natl. Acad. Sci.* USA 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; and Ladner, supra).

Other types of peptide libraries may also be expressed, see, e.g., U.S. Pat. Nos. 5,270,181 and 5,292,646; and PCT publication WO94/02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

If a test compound fails to stimulate the activity of a receptor, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

B. Peptide Libraries

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. As mentioned above, peptide libraries are systems which simultaneously display, in a form which permits interaction with a target, a highly diverse and numerous collection of peptides. Many of the systems known in the art for presentation of peptides in a library are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. Although a cell surface receptor may be used as a target, the screening will not reveal whether the binding of the peptide caused an allosteric change in the conformation of the receptor.

The Ladner et al. patent, U.S. Pat. No. 5,096,815, describes a method of identifying novel proteins or polypeptides with a desired DNA binding activity. Semi-random "variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/02502). The combinatorial peptide can be attached to one of the termini of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library are semi-random, being derived by combinatorial mutagenesis of a known sequence. (See, e.g, Ladner et al. PCT publication WO 90/02909; Garrard et al., PCT publication WO 92/09690; Marks et al. (1992) *J. Biol. Chem.* 267:16007–16010; Griffths et al. (1993) *E.M.B.O.* J 12:725–734; Clackson et al. (1991) *Nature* 352:624–628; and Barbas et al. (1992) *P.N.A.S.* 89:4457–4461). Accordingly, polypeptides which are known ligands for a target receptor can be mutagenized by standard techniques to derive a variegated library of polypeptide sequences which can further be screened for agonists and/or antagonists. This library can be expressed in a reagent cell of the present invention, and other receptor activators can be isolated from the library. This has permitted the identification of even more potent FPRL-1 surrogate ligands (Klein et al., supra).

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter of course will identify potential antagonists of chemoattractant receptors. In still other embodiments, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

C Periplasmic Secretion

In those embodiments of the invention in which yeast cells are used as the host cell and the compounds tested are endogenously expressed from a library, it will be noted that the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Because this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

EXEMPLIFICATION

The invention will be more readily understood by reference to the following examples, which are included merely for purposes of illustration of certain aspects and embodiments of the present invention and are not intended to limit the invention.

Example 1

Fusion Proteins Comprising a Pheromone Sensitive/Responsive Yeast Protein

This example demonstrates the use of recombinant yeast cells incorporating fusion proteins which comprise a chimeric transcription factor operatively linked to a pheromone sensitive/responsive yeast protein to provide a rapid detection assay for stimulation of the pheromone response pathway by an external signal (e.g., a ligand). The chimeric transcription factor comprises a DNA binding domain and a transcriptional activation domain. Principally, any activation domain can be paired with any DNA binding domain to activate transcription. In the present example, the entire prokaryotic protein LexA was used as the DNA binding domain, and an 88 amino acid segment of an acidic E. coli peptide (B42AD) was used as the transcriptional activation domain for the chimeric transcription factor. Both LexA and B42AD were obtained from Clontech Laboratories, Inc. The indicator gene was lacZ which was under the control of 8 copies of LexA operator (p8op-lacZ, Clontech Laboratories, Inc.). This chimeric transcription factor constitutively activates transcription in yeast (data not shown). Expression of the LBF chimeric transcription factor complements fus3 deletion in yeast cells (data not shown). Fus3 was used as the pheromone sensitive yeast protein and was fused downstream of the chimeric transcription factor to generate a LexA-B42AD-Fus3 fusion protein, referred to as "LBF". The gene encoding Fus3 was cloned and sequenced by Fujimura (See Fujimura (1990) Curr. Genet. 18, 395–400). Ligand-activation of G-protein coupled receptors in yeast cells was measured using this LBF chimeric transcription factor plus p8op-lacZ reporter gene construct, as described below.

Construction of Plasmids:

DNA encoding an 88 amino acid fragment of an acidic E. coli peptide that activates transcription in yeast (B42AD) was cloned in pLexA (Clonetech Laboratories, Inc) along with the HA epitope tag for PCR amplification using: Template: pB42AD from Clontech Laboratories, Inc

```
                                       (SEQ ID NO: 1)
Primer1:  CTAGGGATCCGGGAGAGGCATAATCTGGCAC (SEQ ID NO: 2)
Primer2:  GATCGAATTCGGTATCAATAAAGATATCGAGGAGTGC.
```

The resulting PCR product was purified, digested with EcoRI and BamHI and ligated in pLexA (Clontech Laboratories, Inc) that was digested with EcoRI and BamHI enzymes to generate Cp5650: ADH1p-LexA-B42AD-ADHt 2μ HIS3 AmpR.

The FUS3 open reading frame was cloned from yeast genomic DNA using:

```
                                       (SEQ ID NO:3)
Primer3:  GATCGGATCCATGCCAAAGAGAATTGTATACAATATATC (SEQ ID NO:4)
Primer4:  ACGCGTCGACTAACTAAATATTTCGTTCCAAATGAGTTTC
```

The resulting PCR product was digested with BamHI and SalI and ligated into Cp5650 that was digested with BamHI and SalI enzymes to generate Cp5746: ADH1p-LexA-B42AD-FUS3-ADHt 2μ HIS3 AmpR. Cp5746 was then digested with EcoRI and Pst I and the 1.3 kb fragment was isolated and ligated into Cp5545 that was digested with EcoRI and Pst I enzymes to generate Cp5766: ADHp-LexA-B42AD-FUS3-ADHt TRP1 CEN6 ARSH4 AmpR.

Cp5545 (ADHp-LexA-MCS-ADHt TRP1 CEN6 ARSH4 AmpR) was generated by cloning the 203–2685 base pair fragment from pLexA (Clontech Laboratories, Inc.) into pRS414 that was digested with EcoRI and SpeI. Although the construct contains an ADH1p, this promoter can be replaced by other promoters that function in yeast well known to the skilled artisan, examples of other promoters include, but are not limited to, PGK, Gal, Cup1, Fus3, and Ste12.

The LBF construct was used to investigate stimulation of the pheromone response pathway using yeast and mammalian heterologous G-protein coupled receptors. Table 1 shows G-protein coupled receptors that were tested with the LBF construct.

LacZ Assay of Ste2

CY1638 (MATa far 1Δ1442 tbt1-1 fus1-HIS3 trp1 ura3 leu2 his3 suc2) was transformed with pLexAop(x8)-lacZ (Clontech Laboratories, Ltd.) and Cp5766. Transformants were streaked out for single colony purification. A single colony was patched and cells from the patch were frozen down as CY16117. Cells were grown overnight in media lacking uracil and tryptophan. The optical density at 600 nm was determined and the cultures were diluted in fresh media to a final $OD_{600}$ of 0.2. The cultures were then grown for an additional 2 hours and diluted again to an $OD_{600}$ of 0.2. The lacZ enzyme assay was performed in a 96 well plate and each reaction was performed in duplicate in a total volume of 100 μl with 90 μl of culture and 10 μl of the ligand. LacZ activities were measured at the following concentrations of α-factor: 0 pM, 6.0 pm, 30.2 pM, 151 pM, 755 pM, 3.78 nM, 18.9 nM, 94.4 nM, 472 nM, 2.36 μM, 11.8 μM and 59 μM.

Following the addition of ligand, the 96 well plates were incubated at 30° C. for either 1, 2 or 3 hours. 20 μl of 1:1 mixture of 1 mM Fluorescein di-β-D Galactopyranoside (FDG) in 25 mM Pipes, pH 7.2 and 5% Triton X-100 in 250 mM Pipes, pH 7.2 was then added. The reactions were incubated at 37° C. for 90 minutes before being stopped by the addition of 20 μl 1M $Na_2CO_3$ to each well. The plates were read on a fluorometer using an excitation wavelength of 485 nm and an emission wavelength of 535 nm. The data was analyzed using GraphPad Prism software and is summarized in Table 1 below.

LacZ Assay of Melatonin 1a Receptor

CY10981 (MATα GPA1$^+$ sst2Δ2 far 1Δ1442 tbt1-1 fus1-HIS3 can1 ste14::trp1::LYS2 ste3Δ1156 lys2 ura3 leu2 trp1 his3) was transformed with pLexAop(x8)-lacZ, Cp5766, and Cp1289 to create CY16328; with pLexAop(x8)-lacZ, Cp5766, and Cp2695 to create strain CY16330. CY12946 (MATα GPA1-Gαi2(5) sst2Δ2 far1Δ1442 tbt1-1 fus1-HIS3 can1 ste14::trp1::LYS2 ste3Δ1156 lys2 ura3 leu2 trp1 his3) was transformed with the same set to create CY16332 and CY16334.

Cells from each strain were grown overnight in media lacking uracil, tryptophan and leucine, at pH 6.8 with 25 mM PIPES. The optical density of a 1/10 dilution of the overnight cultures was determined at 600 nm and the cultures were diluted in fresh media to a final $OD_{600}$ of 0.2. The cultures were then grown for an additional 1.5 hours and diluted again to an $OD_{600}$ of 0.2. The lacZ enzyme assay was performed in a 96 well plate and each reaction was performed in duplicate in a total volume of 100 μl with 90 μl of culture and 10 μl of ligand. The final concentration of DMSO in each well was kept constant at 1%. LacZ activities, in the presence and absence of the melatonin 1a receptor, were measured at the following concentrations of melatonin: 0 pM, 10 pM, 100 pM, 1 nM, 10 nM, 100 nM, 1 μM, 10 μM, 100 μM and 860 μM.

Following the addition of ligand, the 96 well plates were incubated at 30° C. for either 1, 2 or 3 hours. 20 μl of 1:1 mixture of 1 mM Fluorescein di-β-D Galactopyranoside (FDG) in 25 mM Pipes, pH 7.2 and 5% Triton X-100 in 250 mM Pipes, pH 7.2 was then added. The plates were incubated at 37° C. for 90 minutes before being stopped by adding 20 μl M $Na_2CO_3$ to each well. The plates were read on a fluorometer using an excitation wavelength of 485 nm and an emission wavelength of 535 nm. Table 1 (see below) provides a comparison of the readout obtained using FUS1p-lacZ and the LBF system (plus the p8op-lacZ reporter gene). The data demonstrates that the LBF system produced higher lacZ activities compared with FUS1p-lacZ, despite the lower fold induction. Time course comparison also showed that the LBF assay can produce a readout after a shorter time period of incubation with the ligand compared with the FUS1p-lacZ construct. These results demonstrate that chimeric transcription factors fused to a pheromone sensitive yeast protein can be used to a provide a rapid high throughput screening method.

TABLE 1

A summary of G-Protein Coupled Receptors that have been tested with the LBF system in comparison with FUS1p-lacZ:

| Receptor | Ligand Incubation Time, hrs | Gα | $EC_{50}$ 95% Confidence Interval Fus1p-lacZ | LBF | Maximum Fold Induction Fus1p-lacZ | LBF |
|---|---|---|---|---|---|---|
| Ste2 | 1 | GPA1 | 600 nM–1 μM | 810 nM–1.3 μM | 22 | 29 |
|  | 2 |  | 580 nM–900 nM | 400 nM–700 nM | 123 | 63 |
|  | 3 |  | 850 nM–1.2 μM | 410 nM–640 nM | 218 | 36 |
| Melatonin receptor 1a | 1 | GPA1-i2(5) | 143 nM–3.3 μM | 6.3 nM–30 nM | 54 | 29 |
|  | 2 |  | 6.9 nM–20 nM | 129 pM–242 pM | 197 | 14.3 |
|  | 3 |  | 2.7 nM–6.2 nM | 37 pM–70 pM | 302 | 14.5 |
|  | 1 | GPA1 | 3.4 nM–11 nM | 1.2 nM–4.6 nM | 12 | 8.1 |
|  | 2 |  | 460 pM–1.2 nM | 70 pM–490 pM | 68 | 12 |
|  | 3 |  | 140 pM–450 pM | 38 pM–1.1 nM | 101 | 8.4 |

TABLE 1-continued

A summary of G-Protein Coupled Receptors that have been tested with the LBF system in comparison with FUS1p-lacZ:

| Receptor | Ligand Incubation Time, hrs | Gα | EC₅₀ 95% Confidence Interval Fus1p-lacZ | EC₅₀ 95% Confidence Interval LBF | Maximum Fold Induction Fus1p-lacZ | Maximum Fold Induction LBF |
|---|---|---|---|---|---|---|
| Neurotensin receptor | 1 | GPA1-q(5) | | | 4 | 11.6 |
| | 2 | | 25 nM–35 nM | 11 nM–15 nM | 11 | 23 |
| | 3 | | 25 nM–51 nM | 10 nM–13 nM | 27 | 24 |
| Adenosine receptor 2a | 1 | Gαs D229S | 820 pM–12 nM | 390 pM–6.1 nM | 1.5 | 1.3 |
| | 2 | | 3 nM–11 nM | 6.3 nM–18 nM | 2.7 | 2.4 |
| | 3 | | 4 nM–10 nM | 4.5 nM–9.4 nM | 2.7 | 2.1 |
| Somatostatin receptor 2 | 1 | 41-i2 | | | 1.3 | 1.8 |
| | 2 | | 150 nM–282 nM | 37 nM–416 nM | 1.7 | 1.3 |
| | 3.5 | | 45 nM–68 nM | 34 nM–71 nM | 6 | 2 |
| | 1 | GPA1-i2(5) | 218 nM–580 nM | 107 nM–395 nM | 1.5 | 2.3 |
| | 2 | | 112 nM–246 nM | 76 nM–166 nM | 4.6 | 7.8 |
| | 3.5 | | 58 nM–92 nM | 20 nM–33 nM | 36 | 8.9 |
| Corticotropin releasing factor receptor 1 | 2 | GPA1 | 441 nM–2.6 μM | 10 nM–93 μM | 78 | 12.5 |
| | 4 | | 673 nM–1 μM | 59 nM–1.9 μM | 62 | 4.9 |
| | 2 | Gαs D229S | 283 nM–26 μM | 204 nM–1.1 μM | 16.8 | 6.6 |
| | 4 | | 37 nM–2.8 μM | 14 nM–3.8 μM | 13.3 | 6.3 |

In addition to the alcohol dehydrogenase promoter (ADHp) LBF construct, other constructs were also generated and tested. Three additional constructs, shown in Table 2, were found to be functional in the assays described above, or in similar assays using the GALp-lacZ reporter construct.

TABLE 2

Summary of Additional Chimeric Constructs and their Functionality Determined from lacZ Assay

| Cadus plasmid (Cp) Number | Construct | Function |
|---|---|---|
| 6231 and 6232 | ADHp-LexA-Fus3-B42AD | no |
| 6261 and 6262 | FUS3p-LexA-B42AD-Fus3 | yes |
| 6295 and 6296 | ADHp-Gal4DBD-B42AD-Fus3* | yes |
| 6323 and 6324 | ADHp-Gal4DBD-Gal4ADII-Fus3* | yes |

*The reporter is GALp-lacZ.

In addition to transformation of the chimeric construct, the construct may also be integrated into the yeast strain. For example, Cp5766 was transformed into strain CY7284 (MATa leu2 trp1 his3 ura3 ade2 URA3::LexAop-lacZ), which has LexAop-lacZ integrated. The lacZ assay was performed as described above. After 3 hours of a-factor treatment, β-galactosidase activities increased by 63 fold (data not shown).

Example 2

Production of Mutant Pheromone Sensitive Yeast Proteins

To investigate further the role of chimeric transcription factors and their activation by the pheromone response pathway, mutants of the Fus3 pheromone sensitive yeast protein were generated using PCR mutagenesis. The effect of the mutation in the LBF chimeric construct was investigated using methods outlined in Example 1. Mutant Fus3 was generated by amino acid substitution at position 180 and/or at position 182, or position 42 of the wild type Fus3 and the following mutants in Fus3 were generated in the context of ADHp-LexA-B42AD-Fus3 TRP1 CEN6 ARSH4 AmpR:

Construction of Fus3 Mutants at Residues 180 and/or 182

The region encoding the first 183 amino acids of Fus3 was amplified using:

Template: Cp5766

```
                                          (SEQ ID NO:3)
Primer3:   GATCGGATCCATGCCAAAGAGAATTGTATACAATATATC (SEQ ID NO:5)
Primer5:   CCACAWMTTCCWCCATGCCGCTTTGCTGACC
```

(degenerate oligo)

where W is A or T, and M is A or C

The resulting PCR product was purified, digested with MscI and BamHI, and ligated into Cp5766 that was digested with the same two enzymes. Mutants of Fus3 were identified by sequencing the PCR product using standard sequencing techniques and are summarized in Table 3 below.

Construction of Fus3 Mutant at Residue 42:

The FUS3 open reading frame containing mutation at position 42, which changes a lysine residue to an arginine was produced using:

Template: pGA1903,

```
                                              (SEQ ID NO:3)
Primer3:  GATCGGATCCATGCCAAAGAGAATTGTATACAATATATC (SEQ ID NO:4)
Primer4:  ACGCGTCGACTAACTAAATATTTCGTTCCAAATGAGTTTC
```

The resulting PCR product was digested with BamHI and SalI and ligated into Cp5650 that was digested with the same enzymes to generate Cp6082: ADH1p-LexA-B42AD-FUS3 (K42R)-ADHt 2μ HIS3 AmpR. Cp6082 was subsequently digested with BamHI and MscI and the 555 bp fragment was isolated and ligated into Cp5766 that was digested with the same enzymes to generate Cp6192. Mutation was confirmed by sequencing. Table 3 show mutants of Fus3 generated in the context of ADHp-LexA-B42AD-Fus3 fusion protein.

TABLE 3

Mutants of Fus3 generated in the context of ADHp-LexA-B42AD-Fus3 chimeric construct

| Cadus Plasmid (Cp) Number | Mutation in Fus3 |
|---|---|
| 6182 | Thr180Val, Tyr182Asp |
| 6183 | Thr180Glu |
| 6184 | Thr180Val, Tyr182Val |
| 6185 | Thr180Glu, Tyr182Asp |
| 6187 | Thr180Glu, Tyr182Val |
| 6189 | Thr180Val |
| 6192 | Lys42Arg | pLexAop(x8)-lacZ and one of the above plasmids or Cp5766 were transformed into yeast strain CY17206 (MATa bar1 trp1-1a leu2-3, 112 ura3 ade1 his2) or CY17327 (MATa bar1 trp1-1a leu2-3, 112 ura3 ade1 his2 kss1::LEU2 fus3::ura3Δ5044). Transformants were grown overnight in media lacking uracil and tryptophan. The optical density at 600 nm was determined and the cultures were diluted in fresh media to a final $OD_{600}$ of 0.2. The cultures were then grown for an additional 3 hours and diluted again to an $OD_{600}$ of 0.2. The lacZ enzyme assay was performed in a 96 well plate and each reaction was performed in triplicate in a total volume of 100 μl with 95 μl of culture and 5 μl of 0.1 mg/ml α-factor. Following the addition of ligand, the 96 well plates were incubated at 30° C. for one hour. 20 μl of 1:1 mixture of 1 mM Fluorescein di-β-D Galactopyranoside (FDG) in 25 mM Pipes, pH 7.2 and 5% Triton X-100 in 250 mM Pipes, pH 7.2 was then added. The reactions were incubated at 37° C. for 90 minutes before being stopped by adding 20 μl 1M $Na_2CO_3$ to each well. The plates were read on a fluorometer using an excitation wavelength of 485 nm and an emission wavelength of 535 nm. Table 4 provides a summary of the effect of the mutation in Fus3 of the LBF chimeric construct.

TABLE 4

A summary of the effect of the mutation in Fus3 of the LBF chimeric construct.

| pLexAop(x8)-lacZ and | Mutation in Fus3 | Fold Induction in CY17206 | Fold Induction in CY17327 |
|---|---|---|---|
| Cp5766 | none | 7.1 | 5.5 |
| Cp6182 | Thr180Val Tyr182Asp | 7.5 | 1.0 |
| Cp6183 | Thr180Glu | 8.3 | 0.97 |
| Cp6184 | Thr180Val Tyr182Val | 6.5 | 0.97 |
| Cp6185 | Thr180Glu Tyr182Asp | 4.3 | 0.98 |
| Cp6187 | Thr180Glu Tyr182Val | 6.7 | 1.0 |
| Cp6189 | Thr180Val | 10.7 | 1.0 |
| Cp6192 | Lys42Arg | 9.9 | 1.0 |

All of the above Fus3 mutants in the chimeric construct were functional when transformed into a FUS3⁺ yeast strain, and resulted in activated transcription of the lacZ gene upon α-factor treatment. However, when the Fus3 mutants were transformed into a fus3 null yeast strain, the Fus3 mutants failed to function. These results indicate a requirement for the presence of wild type Fus3 for transcriptional activation of the lacZ gene. The wild type Fus3 may be present endogenously in the yeast cell, or may be part of the chimeric transcription factor.

Example 3

A Chimeric Fusion Protein that Confers Pheromone Dependent Histidine Prototrophy on a Yeast Cell The present example describes the use of a pheromone responsive yeast protein operatively linked to a polypeptide that is required for yeast cell viability. A suitable pheromone responsive yeast protein is, for example, Ste11. The STE11 coding sequence, or a fragment thereof encoding the Ste11 regulatory domain, is fused to a sequence encoding His3 (imidazoleglycerol-phosphate dehydratase), a protein required for cell viability. This chimeric construct is then inserted into a yeast expression vector between the ADH1 promoter and the ADH1 terminator; the vector also contains the TRP1 selectable marker, an autonomous replicating sequence, and the centromere from yeast chromosome VI. Upon transformation into the appropriate yeast strain, (preferably a histidine auxotrophic strain), the constitutively expressed chimeric Ste11-His3 fusion protein confers pheromone pathway-dependent histidine prototrophy on the cell.

The STE11 gene encodes a protein kinase of 738 residues and can be obtained using standard molecular biology techniques. Fusion proteins comprising the Ste11 protein and a protein required for cell viability, e.g., His3, can be prepared as described in Example 1. The Ste11 regulatory domain of Ste11 consists of the N-terminal 415 amino acid residues. Activation of the yeast pheromone pathway causes the phosphorylation of the Ste11 regulatory domain by Ste20, which in turn stimulates Ste11 to phosphorylate the MAP kinase kinase Ste7, leading to MAP kinase (Fus3) activation.

The HIS3 gene encodes imidazoleglycerol-phosphate dehydratase, an enzyme of 219 residues that catalyzes the formation of imidazole acetal-phosphate from imidazoleglycerolphosphate, an essential step in histidine biosynthesis. The fusion of Ste11 or of Ste11ΔC (the amino terminal regulatory domain alone) to the amino terminus of His3 confers pheromone inducibility upon the activity of the His3 enzyme.

The chimeric construct is transformed into an appropriate yeast strain, (preferably a histidine auxotrophic strain). The appropriate yeast strain contains a mammalian receptor gene in a yeast expression vector, a G-protein appropriate to that receptor, a deletion of the endogenous pheromone receptor gene (STE2 or STE3), and a lesion in the endogenous his3 gene, in addition to the expression plasmid for the Ste11-His3 chimera. A competitive inhibitor of His3, 3-amino-1,2,4-triazole, can be used in the yeast media to titrate the basal (unstimulated) levels of His3 activity.

Constitutive expression of the chimeric Ste11-His3 fusion protein confers pheromone pathway-dependent histidine prototrophy on the cell. Thus, a histidine auxotrophic strain that is unable to grow on histidine minus media plates, acquires an ability to grow on these plates upon stimulation of the yeast pheromone pathway.

Incorporation by Reference

All patents, published patent applications and other references disclosed herein are hereby expressly incorporated herein in their entireties by reference.

Equivalents

Those skilled in the art will recognize, or will be able to ascertain using no more than routine experimentation, many equivalents to the specific embodiments of the invention described herein. Such equivalents are intended to be encompassed by the following claims.

What is claimed is:

1. A recombinant yeast cell comprising:
   a mutated Fus3 yeast protein comprising an amino acid substitution at positions 42, 180 or 182, or at positions 180 and 182 as compared to wild type Fus3, and wherein said yeast protein is operatively linked to a chimeric transcription factor;
   a heterologous receptor selected from the group consisting of melatonin receptor 1a, galanin receptor 1, neurotensin receptor, adenosine receptor 2a, somatostatin receptor 2, and corticotropin releasing factor receptor 1, wherein said receptor is functionally integrated into a pheromone response pathway of the yeast cell; and
   a gene which produces a detectable protein, wherein said yeast protein is responsive to said yeast pheromone response pathway of the cell; and wherein the activity of said yeast protein is modulated indirectly upon stimulation of said pathway, and wherein upon modulation of said yeast protein, said chimeric transcription factor causes a detectable signal to be generated.

2. The recombinant yeast cell of claim 1, wherein said gene is an endogenous gene at its natural location in the yeast cell.

3. The recombinant yeast cell of claim 1, wherein said mutated Fus3 yeast protein is derived from said wild type Fus3 yeast protein.

4. The recombinant yeast cell of claim 1, wherein said transcription factor is selected from the group consisting of bacterial, viral and eukaryotic transcription factors.

5. The recombinant yeast cell of claim 1, wherein said chimeric transcription factor comprises a protein selected from the group consisting of Ade1, Ade2, Ade3, Ade4, Ade5, Ade7, Ade8, Asp3, Arg1, Arg3, Arg4, Arg5, Arg6, Arg8, Aro2, Aro7, Bar1, CAT, Cho1, Cys3, Gal1, Gal7, Gal10, GFP, His1, His3, His4, His5, Hom3, Hom6, Ilv1, Ilv2, Ilv5, Ino1, Ino2, Ino4, lacZ, Leu1, Leu2, Leu4, luciferase, Lys2, Mal, Mel, Met2, Met3, Met4, Met8, Met9, Met14, Met16, Met19, Ole1, Pho5, Pro1, Pro3, Thr1, Thr4, Trp1, Trp2, Trp3, Trp4, Trp5, Ura1, Ura2, Ura3, Ura4, Ura5, Ura10, Cdc25, Cyr1 and Ras, or fragment thereof.

6. The recombinant yeast cell of claim 1, wherein said heterologous receptor is melatonin receptor 1a.

7. The recombinant yeast cell of claim 1, wherein said chimeric transcription factor comprises an enzyme.

8. The recombinant yeast cell of claim 7, wherein said enzyme is selected from the group consisting of CAT, Gal1, lacZ, Mel, and Pho5.

9. The recombinant yeast cell of claim 1, wherein said chimeric transcription factor comprises a protein required for cell viability.

10. The recombinant yeast cell of claim 9, wherein said protein required for cell viability is selected from the group consisting of Gal1, His3, Leu2, Mel, Ura3, Cdc25, Cyr1 and Ras.

11. The recombinant yeast cell of claim 1, wherein said transcription factor comprises an indicator molecule.

12. The recombinant yeast cell of claim 11, wherein said indicator molecule is GFP.

13. The recombinant yeast cell of claim 1 further comprising a promoter operatively linked to said gene, such that upon modulation of the activity of said yeast protein, the activity of said chimeric transcription factor is stimulated, thereby activating transcription of said gene that produces said detectable protein.

14. The recombinant yeast cell of claim 13, wherein said promoter comprises the minimal Gal promoter and LexA operators, said gene is lacZ, and said detectable protein is β-galactosidase.

15. The recombinant yeast cell of claim 1, wherein the activity of said mutated Fus3 yeast protein is modulated by wild type Fus3, and wherein the activity of said wild type Fus3 is directly modulated upon stimulation of said pheromone response pathway.

16. The recombinant yeast cell of claim 15, wherein said chimeric transcription factor comprises a LexA DNA binding domain operatively linked to a B42 transcriptional activation domain.

17. The recombinant yeast cell of claim 15, wherein said chimeric transcription factor comprises a Gal4 DNA binding domain operatively linked to a B42 transcriptional activation domain.

18. The recombinant yeast cell of claim 15, wherein said chimeric transcription factor comprises a Gal4 DNA binding domain operatively linked to a VP16 transcriptional activation domain.

19. The recombinant yeast cell of claim 15, wherein said chimeric transcription factor comprises a Gal4 DNA binding domain operatively linked to a Gal4 transcriptional activation domain II.

20. The recombinant yeast cell of claim 1, wherein said transcription factor is a yeast transcription factor.

21. The recombinant yeast cell of claim 20, wherein said transcription factor is selected from the group consisting of Ste12, Gal4, Pho4, Gcn4, Hap1, Adr1, Ace2, Cup2, Swi5 and Bas1.

22. The recombinant yeast cell of claim 21, wherein said transcription factor is Ste12.

23. The recombinant yeast cell of claim 21, wherein said transcription factor is Gal4.

24. The recombinant yeast cell of claim 21, wherein said transcription factor is Pho4.

25. The recombinant yeast cell of claim 1, wherein said chimeric transcription factor comprises a DNA binding domain operatively linked to a transcriptional activation domain.

26. The recombinant yeast cell of claim 25, wherein said DNA binding domain comprises a polypeptide sequence derived from a polypeptide selected from the group consisting of LexA, Gal4, Adr1, Ace2, Cup2, Bas1, Gcn4, Swi5, Pho4, Hap1 and LacI, and wherein said transcriptional activation domain comprises a polypeptide sequence derived from a polypeptide selected from the group consisting of B42, Gal4, Adr1, Ace2, Cup2, Bas1, Gcn4, Swi5, Pho4, Hap1, VP16, and Ste12.

27. The recombinant yeast cell of claim 26, wherein said DNA binding domain comprises a polypeptide sequence derived from LexA.

28. The recombinant yeast cell of claim 26, wherein said DNA binding domain comprises a polypeptide sequence derived from Gal4.

29. The recombinant yeast cell of claim 26, wherein said DNA binding domain comprises a polypeptide sequence derived from Pho4.

30. The recombinant yeast cell of claim 26, wherein said transcriptional activation domain comprises a polypeptide sequence derived from B42.

31. The recombinant yeast cell of claim 26, wherein said transcriptional activation domain comprises a polypeptide sequence derived from VP16.

32. The recombinant yeast cell of claim 26, wherein said transcriptional activation domain comprises a polypeptide sequence derived from Gal4.

33. The recombinant yeast cell of claim 26, wherein said transcriptional activation domain comprises a polypeptide sequence derived from Ste12.

34. The recombinant yeast cell of claim 25, wherein said DNA binding domain and transcriptional activation domain are derived from the same protein.

35. The recombinant yeast cell of claim 34, wherein said chimeric transcription factor comprises a Gal4 DNA binding domain operatively linked to a Gal4 transcriptional activation domain II.

36. The recombinant yeast cell of claim 25, wherein said DNA binding domain and transcriptional activation domain are derived from different proteins.

37. The recombinant yeast cell of claim 36, wherein said chimeric transcription factor comprises a LexA DNA binding domain operatively linked to a B42 transcriptional activation domain.

38. The recombinant yeast cell of claim 36, wherein said chimeric transcription factor comprises a Gal4 DNA binding domain operatively linked to a B42 transcriptional activation domain.

39. The recombinant yeast cell of claim 36, wherein said chimeric transcription factor comprises a Gal4 DNA binding domain operatively linked to a VP16 transcriptional activation domain.

40. The recombinant yeast cell of claim 1, wherein said heterologous receptor is expressed in the membrane of said yeast cell.

41. The recombinant yeast cell of claim 40, further comprising a heterologous test polypeptide, wherein said heterologous test polypeptide is transported to a location allowing interaction with the extracellular region of said heterologous receptor, and wherein said heterologous test polypeptide is expressed at a sufficient level such that modulation of the signal transduction activity of the receptor by the heterologous test polypeptide alters said detectable signal.

42. The recombinant yeast cell of claim 41, wherein said heterologous test polypeptide includes a signal sequence that facilitates transport of the polypeptide to a location allowing interaction with the extracellular region of the receptor.

43. The recombinant yeast cell of claim 1, further comprising a promoter, wherein transcription of said gene is controlled by said promoter.

44. The recombinant yeast cell of claim 43, wherein said promoter is selected from the group consisting of Gal1, Gal10, Mel and LexA operator.

45. The recombinant yeast cell of claim 43, wherein upon modulation of the activity of said yeast protein, said yeast protein activates transcription of said gene that produces said detectable protein.

46. The recombinant yeast cell of claim 45, wherein said detectable protein is selected from the group consisting of α-galactosidase, β-galactosidase, alkaline phosphatase, horseradish peroxidase, exoglucanase, luciferase, Bar1, Pho5 acid phosphatase, green fluorescent protein, chitinase, and chloramphenicol acetyl transferase.

47. The recombinant yeast cell of claim 45, wherein said gene is selected from the group consisting of ADE1, ADE2, ADE3, ADE4, ADE5, ADE7, ADE8, ASP3, ARG1, ARG3, ARG4, ARG5, ARG6, ARG8, ARO2, ARO7, BAR1, CAT, CHO1, CYS3, GAL1, GAL7, GAL10, GFP, HIS1, HIS3, HIS4, HIS5, HOM3, HOM6, ILV1, ILV2, ILV5, INO1, INO2, INO4, lacZ, LEU1, LEU2, LEU4, luciferase, LYS2, MAL, MEL, MET2, MET3, MET4, MET8, MET9, MET14, MET16, MET19, OLE1, PHO5, PRO1, PRO3, THR1, THR4, TRP1, TRP2, TRP3, TRP4, TRP5, URA1, URA2, URA3, URA4, URA5 and URA10.

48. The recombinant yeast cell of claim 47, wherein said gene is selected from the group consisting of CAT, GAL1, GAL7, GAL10, GFP, HIS3, lacZ, luciferase, LEU2, MEL, PHO5, and URA3.

49. A recombinant yeast cell comprising:
a mutated Fus3 yeast protein comprising an amino acid substitution at positions 42, 180 or 182, or at positions 180 and 182 as compared to wild type Fus3, wherein said amino acid substitution is selected from the group consisting of Lys42Arg, Thr180Val, Thr180Glu, Tyr182Val and Tyr182Asp and wherein said yeast protein is operatively linked to a chimeric transcription factor;
a heterologous receptor selected from the group consisting of melatonin receptor 1a, galanin receptor 1, neurotensin receptor, adenosine receptor 2a, somatostatin receptor 2, and corticotropin releasing factor receptor 1, wherein said receptor is functionally integrated into a pheromone response pathway of the yeast cell; and
a gene which produces a detectable protein, wherein said yeast protein is responsive to said yeast pheromone response pathway of the cell; and wherein the activity of said yeast protein is modulated indirectly upon stimulation of said pathway, and wherein upon modulation of said yeast protein, said chimeric transcription factor causes a detectable signal to be generated.

* * * * *